(12) United States Patent
Tahri et al.

(10) Patent No.: US 7,199,148 B2
(45) Date of Patent: Apr. 3, 2007

(54) BROADSPECTRUM SUBSTITUTED OXINDOLE SULFONAMIDE HIV PROTEASE INHIBITORS

(75) Inventors: Abdellah Tahri, Anderlecht (BE); Piet Tom Bert Paul Wigerinck, Terhagen (BE)

(73) Assignee: Tibotec Pharmaceuticals Ltd, County Cork (IE)

( * ) Notice: Subject to any disclaimer, the term of this patent is extended or adjusted under 35 U.S.C. 154(b) by 0 days.

(21) Appl. No.: 10/524,451

(22) PCT Filed: Aug. 14, 2003

(86) PCT No.: PCT/EP03/50379

§ 371 (c)(1),
(2), (4) Date: Feb. 10, 2005

(87) PCT Pub. No.: WO2004/016619

PCT Pub. Date: Feb. 26, 2004

(65) Prior Publication Data

US 2006/0058368 A1    Mar. 16, 2006

(30) Foreign Application Priority Data

Aug. 14, 2002   (EP)   .................... 02078384

(51) Int. Cl.
| | | |
|---|---|---|
| A61K 31/404 | (2006.01) | |
| A61K 31/381 | (2006.01) | |
| A61K 31/34 | (2006.01) | |
| C07D 209/34 | (2006.01) | |
| C07D 209/04 | (2006.01) | |
| C07D 409/02 | (2006.01) | |
| C07D 307/34 | (2006.01) | |

(52) U.S. Cl. ...................... 514/414; 514/444; 514/461; 514/465; 548/487; 548/469; 548/518; 548/516; 549/60; 549/465

(58) Field of Classification Search ................ 548/486; 514/415, 414
See application file for complete search history.

(56) References Cited

FOREIGN PATENT DOCUMENTS

| EP | 0499299 A2 | 8/1992 |
|---|---|---|
| EP | 0499299 B1 | 8/1992 |
| EP | 0721331 B1 | 7/1996 |
| WO | WO 94/05263 A1 | 3/1994 |
| WO | WO 95/06030 A1 | 3/1995 |
| WO | WO 95/09615 A1 | 4/1996 |
| WO | WO 96/22287 A1 | 7/1996 |
| WO | WO 96/28418 A1 | 9/1996 |
| WO | WO 96/28463 A1 | 9/1996 |
| WO | WO 96/28464 A1 | 9/1996 |
| WO | WO 96/28465 A1 | 9/1996 |
| WO | WO 97/18205 A1 | 5/1997 |
| WO | WO 97/44014 A1 | 11/1997 |
| WO | WO 98/42318 A1 | 10/1998 |
| WO | WO 99/33792 A2 | 7/1999 |
| WO | WO 99/33793 A2 | 7/1999 |
| WO | WO 99/33795 A1 | 7/1999 |
| WO | WO 99/33815 A1 | 7/1999 |

(Continued)

OTHER PUBLICATIONS

Goodman, et al., "Biotransformation of Drugs", The Pharmacological Basis of Therapeutics, p. 13-18, 8th Edition, 1990.

(Continued)

*Primary Examiner*—Joseph K. McKane
*Assistant Examiner*—Yong Chu

(57) ABSTRACT

The present invention concerns the compounds having the formula

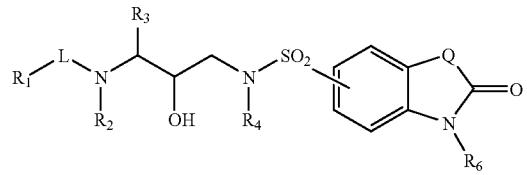

(I)

N-oxides, salts, stereoisomeric forms, racemic mixtures, prodrugs, esters and metabolites thereof, wherein $R_1$ and $R_8$ each are H, optionally substituted $C_{1-6}$alkyl, $C_{2-6}$alkenyl, $C_{3-7}$cycloalkyl, aryl, Het$^1$, Het$^2$; $R^1$ may also be a radical of formula $(R_{11a}R_{11b})NC(R_{10a}R_{10b})CR_9$—; t is 0, 1 or 2; $R_2$ is H or $C_{1-6}$alkyl; L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$; $R_3$ is $C_{1-6}$alkyl, aryl, $C_{3-7}$cycloalkyl, $C_{3-7}$cycloalkyl$C_{1-4}$alkyl, or aryl$C_{1-4}$alkyl; $R_4$ is H, $C_{1-4}$alkylOC(=O), carboxyl, aminoC(=O), mono- or di($C_{1-4}$alkyl)aminoC(=O), $C_{3-7}$cycloalkyl, $C_{2-6}$alkenyl, $C_{2-6}$alkynyl or optionally substituted $C_{1-6}$alkyl;

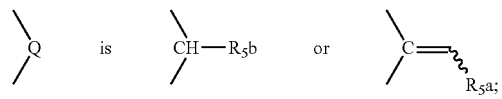

$R_{5a}$ and $R_{5b}$ is $C_{2-6}$alkenyl, $C_{2-6}$alkynyl, $C_{3-7}$cycloalkyl or $C_{1-6}$alkyl, optionally substituted on one or more atoms; $R_{5a}$ and $R_{5b}$ may also be hydrogen, aryl, Het$^1$, Het$^2$; $R_6$ is hydrogen or $C_{1-6}$alkyl optionally substituted on one ore more carbon atoms. It further relates to their use as broad-spectrum HIV protease inhibitors, processes for their preparation as well as pharmaceutical compositions and diagnostic kits comprising them. It also concerns combinations thereof with another anti-retroviral agent, and to their use in assays as reference compounds or as reagents.

15 Claims, No Drawings

FOREIGN PATENT DOCUMENTS

| WO | WO 99/65870 A2 | 12/1999 |
| WO | WO 99/67254 A2 | 12/1999 |
| WO | WO 99/67417 A2 | 12/1999 |
| WO | WO 01/72708 A2 | 10/2001 |

OTHER PUBLICATIONS

Hertogs, et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs", Antimicrobial Agents and Chemotherapy, vol. 42, (1998) pp. 269-276.

Augustijns, et al., "Drug absorption studies of prodrug esters using the Caco-2 model: evaluation of ester hydrolysis and transepithelial transport", International Journal of Pharmaceutics 166, (1998) pp. 44-54.

International Search Report mailed Nov. 26, 2003 for PCT/EP03/50379.

BROADSPECTRUM SUBSTITUTED OXINDOLE SULFONAMIDE HIV PROTEASE INHIBITORS

CROSS REFERENCE TO RELATED APPLICATIONS

This application is the national stage of Application No. PCT/EP03/50379, filed Aug. 14, 2003, which application claims priority from European Patent Application No. 02078384.1 filed Aug. 14, 2002.

This application claims priority benefit to EP Application EP 02078384.1 filed on Aug. 14, 2002, the contents of which are expressly incorporated by reference herein.

The present invention relates to substituted oxindole sulfonamides, their use as broadspectrum HIV protease inhibitors, processes for their preparation as well as pharmaceutical compositions and diagnostic kits comprising them. The present invention also concerns combinations of the present substituted oxindole sulfonamides with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance, with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), nucleotide reverse transcriptase inhibitors (NtRTIs) or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever-increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. On the International AIDS Conference in Paris in July 2003 researchers released that the biggest study so far of resistance to AIDS drugs finds that about 10 percent of all newly infected people in Europe have drug-resistant strains. Smaller tests to determine the spread of resistance have been done in the high-risk city center of San Francisco. This test showed the highest level of resistance at 27 percent. Therefore, there is a need in the art for new compounds for retrovirus therapy, more particularly for AIDS therapy. The need in the art is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One additional way of reducing this pill burden is finding anti-HIV compounds with good bioavailability, i.e. a favorable pharmacokinetic and metabolic profile, such that the daily dose can be minimized and consequently also the number of pills to be taken.

Another favorable characteristic of an anti-HIV compound is that plasma protein binding of the inhibitor has minimal or even no effect on its potency.

Thus, there is a high medical need for protease inhibitors that are able to combat a broad spectrum of mutants of the HIV virus with little variance in fold resistance. Those protease inhibitors with a good bioavailability and little or no effect on their potency due to plasma protein binding have additional advantages.

Up until now, several protease inhibitors are on the market or are being developed. One particular core structure (depicted below) has been disclosed in a number of references, such as, WO 95/06030, WO 96/22287, WO 96/28418, WO 96/28463, WO 96/28464, WO 96/28465 and WO 97/18205. The compounds disclosed therein are described as retroviral protease inhibitors.

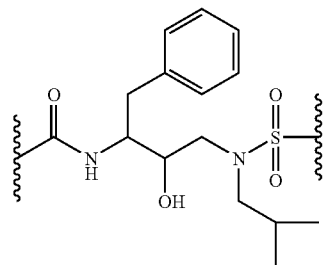

WO 99/67254 discloses 4-substituted-phenyl sulfonamides capable of inhibiting multi-drug resistant retroviral proteases.

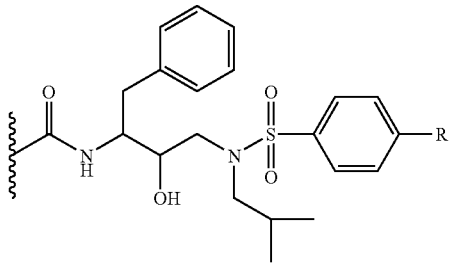

The substituted oxindole sulfonamides of the present invention are found to have a favorable pharmacological profile. Not only are they active against wild-type HIV virus, but they also show a broadspectrum activity against various mutant HIV viruses exhibiting resistance against known protease inhibitors.

The present invention concerns substituted oxindole protease inhibitors, having the formula

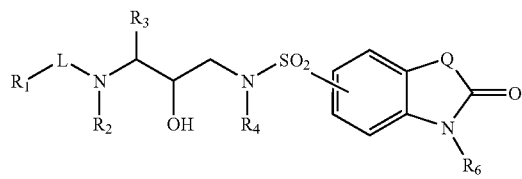

(I)

and N-oxides, salts, stereoisomeric forms, racemic mixtures, prodrugs, esters and metabolites thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1$$C_{1-6}$alkyl, Het$^2$, Het$^2$$C_{1-6}$alkyl;

$R^1$ may also be a radical of formula

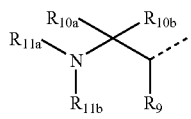

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl;
wherein $R_9$, $R_{10a}$ and the carbon atoms to which they are attached may also form a $C_{3-7}$cycloalkyl radical;
when L is —O—$C_{1-6}$alkanediyl-C(=O)— or —NR$_8$—$C_{1-6}$alkanediyl-C(=O)—, then $R_9$ may also be oxo;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$oxycarbonyl, Het$^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, Het$^1$carbonyl, Het$^1$carbonyloxy, Het$^1$$C_{1-4}$alkyloxycarbonyl, Het$^2$ carbonyloxy, Het$^2$$C_{1-4}$alkylcarbonyloxy, Het$^2$$C_{1-4}$alkyloxycarbonyloxy or $C_{1-4}$alkyl optionally substituted with aryl, aryloxy, Het$^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl;

wherein $R_{11b}$ may be linked to the remainder of the molecule via a sulfonyl group;

t is, each independently, zero, 1 or 2;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$—, wherein either the C(=O) group or the S(=O)$_2$ group is attached to the NR$_2$ moiety; and wherein each independently the $C_{1-6}$alkanediyl moiety may be optionally substituted with hydroxy, aryl, Het$^1$ or Het$^2$;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R^4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-6}$alkyl optionally substituted with one or more substituents each independently selected from aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, mono- or di($C_{1-4}$alkyl)aminosulfonyl, $C_{1-4}$alkylS(=O)$_t$, hydroxy, cyano, halogen or amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl;

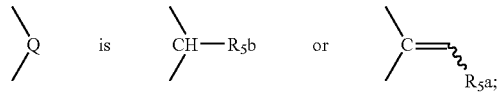

$R_{5a}$ and $R_{5b}$ are, each independently, selected from hydrogen, $C_{1-6}$alkyl, $C_{2-6}$alkenyl, $C_{2-6}$alkynyl, $C_{3-7}$cycloalkyl, aryl, Het$^1$, Het$^2$; wherein each of the substituents selected from $C_{1-6}$alkyl, $C_{2-6}$alkenyl, $C_{2-6}$alkynyl or $C_{3-7}$cycloalkyl is optionally substituted on one or more carbon atoms with a substituent independently selected from the group consisting of amino, mono- or di($C_{1-4}$alkyl)amino, hydroxy, carboxyl, oxo, mercapto, halogen, cyanogen, nitro, $C_{1-4}$alkyloxy, $C_{1-4}$alkylcarbonyl, $C_{1-4}$alkylcarbonyloxy, $C_{1-4}$alkyloxycarbonyl, aryl, $C_{3-7}$cycloalkyl, Het$^1$, Het$^2$, $C_{1-4}$alkylcarbonyloxy, $C_{1-4}$alkyloxycarbonyl;

$R_6$ is hydrogen or $C_{1-6}$alkyl optionally substituted on one ore more carbon atoms with one or more substituents independently selected from the group consisting of amino, mono- or di($C_{1-4}$alkyl)amino, hydroxy, mercapto, oxo, cyanogen, nitro, halogen, carboxyl $C_{1-4}$alkyloxy, $C_{1-4}$alkylcarbonyl, $C_{1-4}$alkylcarbonyloxy, $C_{1-4}$alkyloxycarbonyl, $C_{3-7}$cycloalkyl, aryl, Het$^1$, Het$^2$; wherein each $C_{1-4}$alkyl may optionally be substituted by amino, mono- or di($C_{1-4}$alkyl)amino, hydroxy, mercapto, oxo, cyanogen, nitro, halogen, carboxyl.

A special interest goes to the free base, salt or N-oxide form of the compounds of formula (I), and their stereoisomeric forms.

A mutant of the HIV protease enzyme is defined as an HIV protease enzyme which has at least one mutation in its amino acid sequence relative to the amino acid sequence of the wild-type HIV protease. For purposes of denoting the mutants throughout the text, the HXB2 wild type reference (HIV IIIB LAI wild type), of which the sequence can be found at NIH's GenBank, is used.

The standard of "sensitivity" or alternatively "resistance" of a HIV protease enzyme to a drug is set by the commercially available HIV protease inhibitors. As explained hereinabove, existing commercial HIV protease inhibitors may loose effectivity over time against a population of HIV virus in a patient. The reason being that under pressure of the presence of a particular HIV protease inhibitor, the existing population of HIV virus, usually mainly wild type HIV protease enzyme, mutates into different mutants which a far less sensitive to that same HIV protease inhibitor. If this phenomenon occurs, one talks about resistant mutants. If those mutants are not only resistant to that one particular HIV protease inhibitor, but also to multiple other commercially available HIV protease inhibitors, one talks about multi-drug resistant HIV protease. One way of expressing the resistance of a mutant to a particular HIV protease inhibitor is making the ratio between the $EC_{50}$ of said HIV protease inhibitor against mutant HIV protease over $EC_{50}$ of said HIV protease inhibitor against wild type HIV protease. Said ratio is also called fold resistance (FR).

Many of the mutants occurring in the clinic have a fold resistance of 100 or more against the commercially available HIV protease inhibitors, like saquinavir, indinavir, ritonavir and nelfinavir. Clinically relevant mutants of the HIV protease enzyme can be characterized by a mutation at codon position 10, 71 and/or 84. Examples of such clinical relevant mutant HIV proteases are listed in Table 2.

The compounds of the present invention show a fold resistance ranging between 0.01 and 100 against at least one and in several cases a broad range of clinically relevant mutant HIV proteases. A particular group of compounds of formula (I) are those compounds of formula (I) showing a fold resistance against at least one mutant HIV protease ranging between 0.1 and 100, suitably ranging between 0.1 and 50, and more suitably ranging between 0.1 and 30. Of particular interest are the compounds of formula (I) showing a fold resistance against at least one mutant HIV protease ranging between 0.1 and 20, and even more interesting are those compounds of formula (I) showing a fold resistance against at least one mutant HIV protease ranging between 0.1 and 10.

Thus, the present invention relates to the use of a compound of formula (I) in the manufacture of a medicament useful for inhibiting replication of a HIV virus having a mutant HIV protease, in particular a multi-drug resistant mutant HIV protease. It also relates to the use of a compound of formula (I) in the manufacture of a medicament useful for treating or combating a disease associated with HIV viral infection wherein the protease of the HIV virus is mutant, in particular a multi-drug resistant mutant HIV protease.

In other words, the present invention relates to a method of inhibiting a mutant HIV protease, in particular a multi-drug resistant mutant HIV protease, in a mammal infected with said mutant HIV protease, said method comprising contacting said mutant HIV protease in said mammal with an effective amount of a compound of formula (I). The present invention also relates to a method of inhibiting replication of a HIV virus, which has a mutant HIV protease, in particular a multi-drug resistant mutant HIV protease, in a mammal, said method comprising contacting said HIV virus, which has a mutant HIV protease, in said mammal with an effective amount of a compound of formula (I). The present invention further relates to a method of treating or combating a mammalian disease associated with HIV viral infection wherein the protease of the HIV virus is mutant, in particular a multi-drug resistant mutant HIV protease, said method comprising contacting said HIV virus wherein the protease of the HIV virus is mutant infecting said mammal with an effective amount of a compound of formula (I).

Of particular interest is that the compounds of the present invention can be used in the manufacture of a medicament for the treatment of individuals infected with mutant HIV protease bearing a mutation at least at one of the amino acid positions 10, 71 or 84 or at least a combination of two of these positions or at least a combination of all three.

A basic nitrogen occurring in the present compounds can be quaternized with any agent known to those of ordinary skill in the art including, for instance, lower alkyl halides, dialkyl sulfates, long chain halides and aralkyl halides.

Whenever the term "substituted" is used in defining the compounds of formula (I), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl and 2-methyl-propyl and the like.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{1-6}$alkanediyl" as a group or part of a group defines bivalent straight and branched chained saturated hydrocarbon radicals having from 1 to 6 carbon atoms such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term "$C_{2-6}$alkenyl" as a group or part of a group defines straight and branched chained hydrocarbon radicals having from 2 to 6 carbon atoms containing at least one double bond such as, for example, ethenyl, propenyl, butenyl, pentenyl, hexenyl and the like.

The term "$C_{2-6}$alkynyl" as a group or part of a group defines straight and branched chained hydrocarbon radicals having from 2 to 6 carbon atoms containing at least one triple bond such as, for example, ethynyl, propynyl, butynyl, pentynyl, hexynyl and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include phenyl and naphtyl which both may be optionally substituted with one or more substituents independently selected from $C_{1-6}$alkyl, optionally mono- or disubstituted amino$C_{1-6}$alkyl, $C_{1-6}$alkyloxy, halogen, hydroxy, optionally mono- or disubstituted amino, nitro, cyano, halo$C_{1-6}$alkyl, hydroxy$C_{1-6}$alkyl, carboxyl, $C_{1-6}$alkoxycarbonyl, $C_{1-6}$alkylcarbonyloxy$C_6$alkyl, $C_{1-6}$alkyloxycarbonyl$C_{1-6}$alkyl, $C_{3-7}$cycloalkyl, Het$^1$, Het$^2$, optionally mono- or disubstituted aminocarbonyl, methylthio, methylsulfonyl, and phenyl optionally substituted with one or more substituents each independently selected from $C_{1-6}$alkyl, optionally mono- or disubstituted amino$C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; wherein the optional substituents on any amino function are independently selected from $C_{1-6}$alkyl, $C_{1-6}$alkyloxy-A-, Het$^1$-A-, Het$^1$C$_{1-6}$alkyl, Het$^1$C$_{1-6}$alkyl-A-, Het$^1$oxy-A-, Het$^1$oxyC$_{1-4}$akyl-A-, phenyl-A-, phenyl-oxy-A-, phenyloxyC$_{1-4}$alkyl-A-, phenylC$_{1-6}$alkyl-A-, $C_{1-6}$alkyloxycarbonylamino-A-, amino-A-, aminoC$_{1-6}$alkyl and aminoC$_{1-6}$alkyl-A- wherein each of the amino groups may optionally be mono- or where possible di-substituted with $C_{1-4}$alkyl and wherein A is defined as $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; wherein the point of attachment of A to the nitrogen atom is the $C_{1-6}$alkanediyl group in those moieties containing said group.

The term "halo$C_{1-6}$alkyl" as a group or part of a group is defined as $C_{1-6}$alkyl substituted with one or more halogen atoms, preferably, chloro or fluoro atoms, more preferably fluoro atoms. Preferred halo$C_{1-6}$alkyl groups include for instance trifluoromethyl and difluoromethyl.

The term "hydroxy$C_{1-6}$alkyl" as a group or part of a group is defined as $C_{1-6}$alkyl substituted with one or more hydroxy moieties.

The term "Het$^1$" as a group or part of a group is defined as a saturated or partially unsaturated monocyclic, bicyclic or tricyclic heterocycle having 3 to 14 ring members, preferably 5 to 10 ring members and more preferably 5 to 8 ring members, which contains one or more heteroatom ring members, each independently selected from nitrogen, oxygen and sulfur and which is optionally substituted on one or more carbon atoms by $C_{1-6}$alkyl, optionally mono- or disubstituted amino$C_{1-6}$alkyl, $C_{1-6}$alkyloxy, halogen, hydroxy, oxo, optionally mono- or disubstituted amino, nitro, cyano, halo$C_{1-6}$alkyl, hydroxy$C_{1-6}$alkyl, carboxyl, $C_{1-6}$alkoxycarbonyl, $C_{1-6}$alkylcarbonyloxy$C_{1-6}$alkyl, $C_{1-6}$alkyloxycarbonyl$C_{1-6}$alkyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 14 ring members which contains one or more heteroatom ring members, each independently selected from nitrogen, oxygen or sulfur, and wherein the optional substituents on any amino function are independently selected from $C_{1-6}$alkyl, $C_{1-6}$alkyloxy-A-, Het$^2$-A-, Het$^2$C$_{1-6}$alkyl, Het$^2$C$_{1-6}$alkyl-A-, Het$^2$ oxy-A-, Het$^2$oxyC$_{1-4}$akyl-A-, aryl-A-, aryloxy-A-, aryloxyC$_{1-4}$alkyl-A-, arylC$_{1-6}$alkyl-A-, $C_{1-6}$alkyloxycarbonylamino-A-, amino-A-, aminoC$_{1-6}$alkyl and aminoC$_{1-6}$alkyl-A- wherein each of the amino groups may optionally be mono- or where possible di-substituted with $C_{1-4}$alkyl and wherein A is as defined above.

The term "Het$^2$" as a group or part of a group is defined as an aromatic monocyclic, bicyclic or tricyclic heterocycle having 3 to 14 ring members, preferably 5 to 10 ring members and more preferably 5 to 6 ring members, which contains one or more heteroatom ring members each independently selected from nitrogen, oxygen or sulfur and which is optionally substituted on one or more carbon atoms by $C_{1-6}$alkyl, optionally mono- or disubstituted amino$C_{1-6}$alkyl, $C_{1-6}$alkyloxy, halogen, hydroxy, optionally mono- or disubstituted amino, nitro, cyano, halo$C_{1-6}$alkyl, hydroxy$C_{1-6}$ alkyl, carboxyl, $C_{1-6}$alkoxycarbonylyl, $C_{1-6}$alkylcarbonyloxy$C_{1-6}$alkyl, $C_{1-6}$alkyloxycarbonyl$C_{1-6}$alkyl, $C_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 14 ring members; wherein the optional substituents on any amino function are independently selected from $C_{1-6}$alkyl, $C_{1-6}$alkyloxy-A-, Het$^1$-A-, Het$^1$C$_{1-6}$alkyl, Het$^1$C$_{1-6}$ alkyl-A-, Het$^1$oxy-A-, Het$^1$oxyC$_{1-4}$akyl-A-, aryl-A-, aryloxy-A-, aryloxyC$_{1-4}$alkyl-A-, arylC$_{1-6}$alkyl-A-, $C_{1-6}$alkyloxycarbonylamino-A-, amino-A-, aminoC$_{1-6}$alkyl and aminoC$_{1-6}$alkyl-A- wherein each of the amino groups may optionally be mono- or where possible di-substituted with $C_{1-4}$alkyl and wherein A is as defined above.

As used herein, the term (=O) forms a carbonyl moiety with the carbon atom to which it is attached. The term (=O) forms a sulfoxide with the sulfur atom to which it is attached. The term (=O)$_2$ forms a sulfonyl with the sulfur atom to which it is attached.

As used herein, the term (=S) forms a thiocarbonyl moiety with the carbon atom to which it is attached.

As used herein before, the term "one or more" covers the possibility of all the available C-atoms, where appropriate, to be substituted, preferably, one, two or three.

When any variable (e.g. halogen or $C_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13–15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least two asymmetric centers and thus may exist as different stereoisomeric forms. These two asymmetric centers are indicated with an asterisk (*) in the figure below.

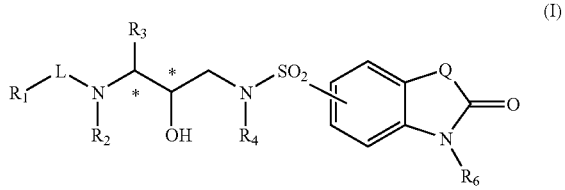

(I)

The absolute configuration of each asymmetric center that may be present in the compounds of formula (I) may be indicated by the stereochemical descriptors R and S, this R and S notation corresponding to the rules described in Pure Appl. Chem. 1976, 45, 11–30. The carbon atom bearing the hydroxy group and marked with the asterisk (*) preferably has the R configuration. The carbon atom bearing the $R^3$ group and marked with the asterisk (*) preferably has the S configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues.

A particular group of compounds are those compounds of formula (I) wherein one or more of the following restrictions apply:

$R_1$ is hydrogen, $Het^1$, $Het^2$, aryl, $Het^1C_{1-6}$alkyl, $Het^2C_{1-6}$alkyl, $arylC_{1-6}$alkyl; more in particular, $R_1$ is hydrogen, a saturated or partially unsaturated monocyclic or bicyclic heterocycle having 5 to 8 ring members, which contains one or more heteroatom ring members, each independently selected from nitrogen, oxygen or sulfur and which is optionally substituted, phenyl optionally substituted with one or more substituents, an aromatic monocyclic heterocycle having 5 to 6 ring members, which contains one or more heteroatom ring members, each independently selected from nitrogen, oxygen or sulfur and which is optionally substituted on one or more carbon atoms, or $C_{1-6}$alkyl substituted with an aromatic monocyclic heterocycle having 5 to 6 ring members, which contains one or more heteroatom ring members, each independently selected from nitrogen, oxygen or sulfur and which is optionally substituted on one or more carbon atoms;

$R_2$ is hydrogen;

L is —C(=O)—, —O—C(=O)—, —O—$C_{1-6}$alkanediyl-C(=O)—, more in particular, L is —C(=O)—, —O—C(=O)—, —O—CH$_2$—C(=O)—, wherein the C(=O) group is attached to the NR$_2$ moiety;

$R_3$ is aryl$C_{1-4}$alkyl, in particular, arylmethyl, more in particular phenylmethyl;

$R_4$ is optionally substituted $C_{1-6}$alkyl, in particular $C_{1-6}$alkyl optionally substituted with aryl, $Het^1$, $Het^2$, $C_{3-7}$cycloalkyl or amino optionally mono- or disubstituted where the substituents are each independently selected from $C_{1-4}$alkyl, aryl, $Het^1$ and $Het^2$;

Q is >C=C—$R_{5a}$ wherein $R_{5a}$ is aryl, $Het^1$, $He^2$; wherein each of said substituents is optionally substituted on one or more atoms with a substituent independently selected from the group consisting of amino, mono- or di($C_{1-4}$alkyl)amino, hydroxy, $C_{1-6}$alkyloxy, carboxyl, oxo, $C_{1-6}$alkyl, hydroxy$C_{1-6}$alkyl, $C_{1-4}$alkylcarbonyloxy, $C_{1-4}$alkyloxycarbonyl, $C_{1-4}$alkylcarbonyloxy$C_{1-4}$alkyl, $C_{1-4}$alkyloxycarbonyl $C_{1-4}$alkyl, $Het^2$; $R_{5a}$ may also be $C_{1-6}$alkyl optionally further substituted with amino, mono- or di($C_{1-4}$alkyl)amino, hydroxy, $C_{1-6}$alkyloxy, carbonyl, oxo, mercapto, $C_{1-4}$alkylcarbonyloxy, $C_{1-4}$alkyloxycarbonyl;

Q is >C=C—$R_{5b}$ wherein $R_{5b}$ is hydrogen; and $R_6$ is hydrogen.

A special group of compounds are those compounds of formula (I) wherein, $R_2$ is hydrogen;

L is —C(=O)—, —O—C(=O)—, —O—CH$_2$—C(=O)—, wherein the C(=O) group is attached to the NR$_2$ moiety;

$R_3$ is phenylmethyl; and $R_4$ is $C_{1-6}$alkyl; and

Q is >C=C—$R_{5a}$ wherein $R_{5a}$ is $Het^1$, aryl, $Het^2$; wherein each of said substituents is optionally substituted on one or more atoms with a substituent independently selected from the group consisting of amino, mono- or di($C_{1-4}$alkyl)amino, hydroxy, $C_{1-6}$alkyloxy, amino$C_6$alkyl, mono- or di($C_{1-4}$alkyl)amino$C_{1-4}$alkyl, carboxyl, oxo, $C_{1-6}$alkyl, hydroxy$C_{1-6}$alkyl, mercapto, $C_{1-4}$alkylcarbonyloxy, $C_{1-4}$alkyloxycarbonyl, $C_{1-4}$alkylcarbonyloxy$C_{1-4}$alkyl, $C_{1-4}$alkyloxycarbonyl$C_{1-4}$alkyl, $C_{3-7}$cycloalkyl, aryl, $Het^1$, $Het^2$.

Another special group of compounds are those compounds of formula (I) wherein, $R_2$ is hydrogen;

L is —C(=O)—, —O—C(=O)—, —O—CH$_2$—C(=O)—, wherein the C(=O) group is attached to the NR$_2$ moiety;

$R_3$ is phenylmethyl;

$R_4$ is $C_{1-6}$alkyl; and

Q is >C=C—$R_{5a}$ wherein $R_{5a}$ is aryl, optionally substituted on one or more atoms with a substituent independently selected from the group consisting of amino, mono- or di($C_{1-4}$alkyl)amino, hydroxy, $C_{1-6}$alkyloxy, amino$C_{1-6}$alkyl, mono- or di($C_{1-4}$alkyl)amino$C_{1-4}$alkyl, carboxyl, oxo, $C_{1-6}$alkyl, hydroxy$C_{1-6}$alkyl, mercapto, $C_{1-4}$alkylcarbonyloxy, $C_{1-4}$alkyloxycarbonyl, $C_{1-4}$alkylcarbonyloxy $C_{1-4}$alkyl, $C_{1-4}$alkyloxycarbonyl $C_{1-4}$alkyl, $C_{3-7}$cycloalkyl, aryl, $Het^1$, $Het^2$.

Yet another special group of compounds are those compounds of formula (I) wherein, $R_2$ is hydrogen;

L is —C(=O)—, —O—C(=O)—, —O—CH$_2$—C(=O)—, wherein the C(=O) group is attached to the NR$_2$ moiety;

$R_3$ is phenylmethyl; and $R_4$ is $C_{1-6}$alkyl; and

Q is >C=C—$R_{5b}$ wherein $R_{5b}$ is hydrogen.

Another interesting group of compounds are those of formula (I) wherein, $R_2$ is hydrogen;

L is —C(=O)—, —O—C(=O)—, —O—CH$_2$—C(=O)—, wherein the C(=O) group is attached to the NR$_2$ moiety;

$R_3$ is phenylmethyl;

$R_4$ is $C_{1-6}$alkyl; and

Q is >C=C—$R_{5a}$ wherein $R_{5a}$ is $Het^2$ optionally substituted on one or more atoms with a substituent independently selected from the group consisting of amino, mono- or di($C_{1-4}$alkyl)amino, hydroxy, $C_{1-6}$alkyloxy, amino$C_{1-6}$alkyl, mono- or di($C_4$alkyl)amino$C_{1-6}$alkyl, carboxyl, oxo, $C_{1-6}$alkyl, hydroxy$C_{1-6}$alkyl, mercapto, $C_{1-4}$alkylcarbonyloxy, $C_{1-4}$alkyloxycarbonyl, $C_{1-4}$alkylcarbonyloxy $C_{1-4}$alkyl, $C_{1-4}$alkyloxycarbonyl $C_{1-4}$alkyl.

Another particular group are those compounds of formula (I), wherein, $R_2$ is hydrogen;

L is —C(=O)—, —O—C(=O)—, —O—CH$_2$—C(=O)—, wherein the C(=O) group is attached to the NR$_2$ moiety;

$R_3$ is phenylmethyl;

$R_4$ is $C_{1-6}$alkyl; and

Q is >C=C—$R_{5a}$ wherein $R_{5a}$ is alkyl optionally substituted on one or more atoms with a substituent independently selected from the group consisting of amino, mono- or di($C_{1-4}$alkyl)amino, hydroxy, $C_{1-6}$alkyloxy, carboxyl, oxo, $C_{1-4}$alkylcarbonyloxy, $C_{1-4}$alkyloxycarbonyl, $C_{3-7}$cycloalkyl, aryl, $Het^1$, $Het^2$.

Another interesting group of compounds are those compounds of formula (I) wherein L is —O—$C_{1-6}$alkanediyl-C(=O)—.

Another group of compounds are those compounds of formula (I) wherein Q is >C=C—$R_{5a}$ wherein $R_{5a}$ is $C_{1-6}$alkyl, aryl, or $Het^2$; each optionally substituted on one or more atoms with a substituent independently selected from the group consisting of amino, mono- or di($C_{1-4}$alkyl)amino, hydroxy, $C_{1-4}$alkyloxy, carboxyl, oxo, sulfhydryl, $C_{1-4}$alkylcarbonyloxy, $C_{1-4}$alkyloxycarbonyl, $C_{3-7}$cycloalkyl, aryl, Het$^1$ and Het$^2$.

Yet another group of compounds are those compounds of formula (I) or any subgroup thereof wherein Q is >C—$R_{5b}$ wherein $R_{5b}$ is hydrogen.

A special group of compounds are those compounds of formula (I) wherein $R_1$-L is Het$^1$-O—C(=O), Het$^2$-$C_{1-6}$ alkanediyl-O—C(=O), aryl-O—$C_{1-6}$alkanediyl-C(=O) or aryl-C(=O).

Of particular interest are those compounds of formula (I) wherein $R_1$ is hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2C_{1-6}$alkyl, in particular, $R_1$ is hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^2$, Het$^2C_{1-6}$alkyl.

An interesting group of compounds are those compounds of formula (I) wherein $R_1$ is hydrogen, $C_{1-6}$alkyl, $C_{2-6}$alkenyl, aryl$C_{1-6}$alkyl, $C_{3-7}$cycloalkyl, $C_{3-7}$cycloalkyl-$C_{1-6}$alkyl, aryl, Het$^1$, Het$^1C_{1-6}$alkyl, Het$^2$, Het$^2C_{1-6}$alkyl; wherein Het$^1$ has 5 or 6 ring members, which contains one or more heteroatom ring members selected from nitrogen, oxygen or sulfur and which is optionally substituted on one or more ring members.

A preferred group of compounds are those compounds where the sulfonamide group is attached to the oxindole group in the 6-position.

A suitable group of compounds are those compounds of formula (I) wherein $R_1$ is aryl or aryl$C_{1-6}$alkyl; in particular the aryl moiety of the $R_1$ definition is further substituted on one or more ring members, wherein each substituent is independently selected from $C_{1-4}$alkyl, hydroxy, halogen, optionally mono- or di($C_{1-4}$alkyl)amino, optionally mono- or di($C_{1-4}$alkyl)amino$C_4$alkyl, nitro and cyanogen; preferably the substituent is selected from methyl, ethyl, chlorine, iodine, bromine, hydroxy and cyanogens, in particular the aryl moiety contains 6 to 12 ring members, more in particular the aryl moiety in the definition of $R_1$ contains 6 ring members.

A suitable group of compounds are those compounds of formula (I) wherein $R_1$ is Het$^2$ or Het$^2C_{1-6}$alkyl, wherein the Het$^2$ in the definition of $R_1$ contains one or more heteroatoms each independently selected from nitrogen, oxygen and sulfur; in particular the Het$^2$ moiety of the $R_1$ definition is further substituted on one or more ring members, wherein each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogen.

Another group of compounds are those of formula (I) wherein $R_1$ is Het$^2$ or Het$^2C_{1-6}$alkyl, L is —C(=O)—, —O—C(=O)—, —O—$C_{1-6}$alkanediyl-C(=O)—; in particular the Het$^2$ moiety in the definition of $R_1$ is an aromatic heterocycle having 5 or 6 ring members, which contain one or more heteroatom ring members each independently selected from nitrogen, oxygen or sulfur, more in particular the Het$^2$ moiety is an aromatic heterocycle having 5 or 6 ring members, which contain two or more heteroatom ring members each independently selected from nitrogen, oxygen or sulfur.

A suitable group of compounds are those compounds of formula (I) wherein $R_1$ is Het$^1$ or Het$^1C_{1-6}$alkyl, wherein Het$^1$ in the definition of $R_1$ contains one or more heteroatoms each independently selected from nitrogen, oxygen and sulfur; in particular the Het$^1$ moiety of the definition of $R_1$ is further substituted on one or more ring members, wherein each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogen.

A suitable group of compounds are those compounds of formula (I) wherein $R_1$ is Het$^1C_{1-6}$alkyl, Het$^1$, wherein said Het$^1$ in the definition of $R_1$ is monocyclic having 5 or 6 ring members, wherein the Het$^1$ contains one or more heteroatoms each independently selected from nitrogen, oxygen and sulfur; in particular the Het$^1$ moiety of the $R_1$ definition is further substituted on one or more carbon atoms, wherein each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogen.

A suitable group of compounds are those compounds of formula (I) wherein $R_1$ is Het$^1$, wherein said Het$^1$ is bicyclic having 7 to 10 ring members, wherein the Het$^1$ contains one or more heteroatoms each independently selected from nitrogen, oxygen and sulfur; in particular the Het$^1$ moiety of the $R_1$ definition is further substituted on one or more carbon atoms, wherein each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogens, in particular the Het$^1$ moiety contains 2 or more heteroatoms selected from nitrogen, sulfur and oxygen; in one aspect $R_1$ is a bicyclic Het$^1$ containing containing at one oxygen heteroatom, L is selected from —O—(C=O)— and Q is >C=C—$R_{5a}$ with $R_{5a}$ and $R_6$ are hydrogen.

A suitable group of compounds are those compounds of formula (I) wherein $R_1$ is Het$^1$, wherein said Het$^1$ is a satured bicyclic group having 5 to 10 ring members, wherein the Het$^1$ contains one or more heteroatoms each independently selected from nitrogen, oxygen and sulfur; in particular the Het$^1$ moiety of the $R_1$ definition is further substituted on one or more carbon atoms, wherein each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogens; in particular Het$^1$ contains 5 to 8 ring members; in particular the Het$^1$ moiety has 6 to 8 ring members wherein Het$^1$ contains 2 or more heteroatoms selected from nitrogen, sulfur and oxygen.

A suitable group of compounds are those compounds of formula (I) wherein $R_1$-L- is bis-tetrahydrofurane-O—C(=O)—.

An interesting group of compounds are those compounds of formula (I) wherein $R_1$ is G or G-$C_{1-6}$alkyl, wherein G is selected from thiazolyl, imidazolyl, oxazolyl, oxadiazolyl, dioxazolyl, pyrazolyl, pyrazinyl, imidazolinonyl, quinolinyl, isoquinolinyl, indolyl, pyridazinyl, pyridinyl, pyrrolyl, pyranyl, pyrimidinyl, furanyl, triazolyl, tetrazolyl, benzofuranyl, benzoxazolyl, isoxazolyl, isothiazolyl, thiadiazolyl, thiophenyl, tetrahydrofurofuranyl, tetrahydropyranofuranyl, benzothiophenyl, carbazoyl, imidazolonyl, oxazolonyl, indolizinyl, triazinyl, quinoxalinyl, piperidinyl, piperazinyl, morpholinyl, thiamorpholinyl, pyrazinyl, thienyl, tetrahydroquinolinyl, tetrahydroisoquinolinyl, β-carbolinyl, dioxanyl, dithianyl, oxolanyl, dioxolanyl, tetrahydrothiophenyl, tetrahydropyranyl, tetrahydropyranyl; wherein G is optionally benzofused; wherein G is optionally further substituted on one or more ring members; preferably G is selected from thiazolyl, imidazolyl, oxazolyl, oxadiazolyl, pyrazolyl, pyridinyl, optionally substituted on one or more ring members.

Interesting compounds are those compounds of formula (I) wherein $R_1$ is hexahydrofuro[2,3-b]furanyl or oxazolyl.

Other interesting compounds are those compounds of formula (I) or those compounds belonging to any subgroup thereof wherein $R_1$ is hexahydrofuro[2,3-b]furanyl, tetrahydrofuranyl, oxazolyl, thiazolyl, and L is a direct bond.

Yet other interesting compounds are those compounds of formula (I) or those compounds belonging to any subgroup thereof wherein $R_1$ is hexahydrofuro[2,3-b]furanyl, oxazolyl, thiazolyl, pyridinyl, or phenyl optionally substituted with one or more substituents independently selected from $C_{1-6}$alkyl, hydroxy, amino, halogen, amino$C_{1-4}$alkyl and mono-or di($C_{1-4}$alkyl)amino; and L is —O—.

Still other interesting compounds are those compounds of formula (I) or those compounds belonging to any subgroup thereof wherein $R_1$ is hexahydrofuro[2,3-b]furanyl, tetrahydrofuranyl, oxazolyl, or phenyl substituted with one or more substituents independently selected from $C_{1-6}$alkyl, hydroxy, amino, halogen, amino$C_{1-4}$alkyl and mono-or di($C_{1-4}$alkyl)amino; and L is $C_{1-6}$alkanediyl-O— wherein the —O— is attached to the nitrogen of the amide.

Also interesting compounds are those compounds of formula (I) or those compounds belonging to any subgroup thereof wherein $R_1$ is hexahydrofuro[2,3-b]furanyl, tetrahydrofuranyl, oxazolyl, thiazolyl, pyridinyl, or phenyl optionally substituted with one or more substituents independently selected from hydroxy, amino, halogen, amino$C_{1-4}$alkyl and mono-or di($C_{1-4}$alkyl)amino; and L is —O—$C_{1-6}$alkanediyl wherein —O— is attached to the $R_1$ group.

Compounds of particular interest are those compounds of formula (I) or those compounds belonging to any subgroup thereof wherein -L-$R^1$ is —O-(hexahydrofuro[2,3-b]furanyl), —O-tetrahydrofuranyl, —O-methyl-(optionally substituted phenyl), —O-methyl-pyridinyl, —O-methyl-thiazolyl, —O-methyl-oxazolyl, -methyl-O-(optionally substituted phenyl) or optionally substituted phenyl. Preferably, the optional substituents on the phenyl group are methyl, amino, hydroxy, halogen, aminomethyl, Compounds of special interest are those compounds of formula (I) or those compounds belonging to any subgroup thereof wherein $R_1$ is hexahydrofuro[2,3-b]furanyl, tetrahydrofuranyl, oxazolyl, thiazolyl, pyridinyl, or phenyl optionally substituted with one or more substituents independently selected from $C_{1-6}$alkyl, hydroxy, amino, chloro, bromo, amino$C_{1-4}$alkyl and mono-or di($C_{1-4}$alkyl)amino.

Another special subgroup of the compounds of formula (I) or of the compounds belonging to any subgroup thereof are those compounds wherein -L-$R^1$ is —O—(hexahydrofuro[2,3-b]furanyl), —O-tetrahydrofuranyl, —O-methyl-thiazolyl, —O—methyl-oxazolyl, -methyl-O-(2,6-dimethylphenyl), -methyl-O-(4-aminomethyl-2,6-dimethyl phenyl), - methyl-O-(4-amino-2,6-dimethylphenyl), 3-hydroxy-2-methyl-phenyl or 3-amino-2-methyl-phenyl; and Q is >C=C—$R_{5a}$ with $R_{5a}$ is methyl or hydrogen and $R^6$ is hydrogen.

A suitable group of compounds are those compounds of formula (I) as a salt, wherein the salt is selected from trifluoroacetate, fumarate, chloroacetate and methanesulfonate.

An interesting group of compounds are those compounds of formula (I) having a fold resistance, determined according to the methods herein described, in the range of 0.01 to 100 against HIV species having at least one mutation in the HIV protease as compared to the wild type sequence (e.g. M38432, K03455, gi 327742) at a position selected from 10, 71 and 84; in particular at least two mutations selected from 10, 71 and 84 are present in the HIV protease; in particular the compounds have a fold resistance in the range of 0.1 to 100, more in particular in the range 0.1 to 50, suitably in the range 0.1 to 30. Of particular interest are the compounds of formula (I) showing a fold resistance against at least one mutant HIV protease ranging between 0.1 and 20, and even more interesting are those compounds of formula (I) showing a fold resistance against at least one mutant HIV protease ranging between 0.1 and 10. Interesting compounds have in addition an $IC_{50}$ of at least 100 nM vis-à-vis the wild type virus upon in vitro screening according to the methods described herein.

Preferred compounds are those enantiomeric forms of the compounds of formula (I) or of the compounds belonging to any subgroup thereof having a (1S,2R)-1-benzyl-2-hydroxypropyl configuration.

An interesting group of compounds of formula (I) are those compounds wherein $R_{5b}$ is hydrogen.

| Most preferred compounds are | |
|---|---|
| (1-Benzyl-2-hydroxy-3-{isobutyl-[2-oxo-3-(1H-pyrrol-2-ylmethylene)-2,3-dihydro-1H-indole-5-sulfonyl]-amino}-propyl)-carbamic acid hexahydrofuro[2,3-b]furan-3-yl ester | (1-Benzyl-2-hydroxy-3-{isobutyl-[2-oxo-3-(4-pyridin-2-yl-benzylidene)-2,3-dihydro-1H-indole-5-sulfonyl]-amino}-propyl)-carbamic acid hexahydro-furo[2,3-b]furan-3-yl ester |
| (1-Benzyl-2-hydroxy-3-{isobutyl-[3-(5-methyl-furan-2-ylmethylene)-2-oxo-2,3-dihydro-1H-indole-5-sulfonyl]-amino}-propyl)-carbamic acid hexahydro-furo[2,3-b]furan-3-yl ester | (1-Benzyl-2-hydroxy-3-{[3-(4-hydroxy-3,5-dimethyl-benzylidene)-2-oxo-2,3-dihydro-1H-indole-5-sulfonyl]-iso butyl-amino}-propyl)-carbamic acid hexahydro-furo[2,3-b]furan-3-yl ester |
| (1-Benzyl-2-hydroxy-3-{isobutyl-[3-(5-methyl-thiophen-2-ylmethylene)-2-oxo-2,3-dihydro-1H-indole-5-sulfonyl]-amino}-propyl)-carbamic acid hexahydro-furo[2,3-b]furan-3-yl ester | (1-Benzyl-3-{[3-(4-dimethylamino-benzylidene)-2-oxo-2,3-dihydro-1H-indole-5-sulfonyl]-isobutyl-amino}-2-hydroxy-propyl)-carbamic acid hexahydro-furo[2,3-b]furan-3-yl ester |
| (1-Benzyl-2-hydroxy-3-{isobutyl-[3-(1-methyl-1H-pyrrol-2-ylmethylene)-2-oxo-2,3-dihydro-1H-indole-5-sulfonyl]-amino}-propyl)-carbamic acid hexahydro-furo[2,3-b]furan-3-yl ester | (1-Benzyl-2-hydroxy-3-{[3-(1H-indol-2-ylmethylene)-2-oxo-2,3-dihydro-1H-indole-5-sulfonyl]-isobutyl-amino}-propyl)-carbamic acid hexahydro-furo[2,3-b]furan-3-yl ester |

-continued

| Most preferred compounds are | |
|---|---|
| (1-Benzyl-3-{[3-(2-ethyl-butylidene)-2-oxo-2,3-dihydro-1H-indole-5-sulfonyl]-isobutyl-amino}-2-hydroxy-propyl)-carbamic acid hexahydro-furo[2,3-b]furan-3-yl ester | Acetic acid 5-(5-{[3-(hexahydro-furo[2,3-b]furan-3-yloxycarbonylamino)-2-hydroxy-4-phenyl-butyl]-isobutyl-sulfamoyl}-2-oxo-1,2-dihydro-indol-3-ylidenemethyl)-furan-2-ylmethyl ester |
| {1-Benzyl-2-hydroxy-3-[isobutyl-(3-isobutylidene-2-oxo-2,3-dihydro-1H-indole-5-sulfonyl)-amino]-propyl}-carbamic acid hexahydro-furo[2,3-b]furan-3-yl ester | {1-Benzyl-3-[(3-benzylidene-2-oxo-2,3-dihydro-1H-indole-5-sulfonyl)-isobutyl-amino]-2-hydroxy-propyl}-carbamic acid hexahydro-furo[2,3-b]furan-3-yl ester |
| {1-Benzyl-3-[(3-furan-2-ylmethylene-2-oxo-2,3-dihydro-1H-indole-5-sulfonyl)-isobutyl-amino]-2-hydroxy-propyl}-carbamic acid hexahydro-furo[2,3-b]furan-3-yl ester | (1-Benzyl-3-{[3-(4-diethylamino-3-hydroxy-benzylidene)-2-oxo-2,3-dihydro-1H-indole-5-sulfonyl]-isobutyl-amino}-2-hydroxy-propyl)-carbamic acid hexahydro-furo[2,3-b]furan-3-yl ester |
| (1-Benzyl-2-hydroxy-3-{isobutyl-[3-(4-methoxy-benzylidene)-2-oxo-2,3-dihydro-1H-indole-5-sulfonyl]-amino}-propyl)-carbamic acid hexahydro-furo[2,3-b]furan-3-yl ester | (1-Benzyl-2-hydroxy-3-{[3-(2-hydroxy-benzylidene)-2-oxo-2,3-dihydro-1H-indole-5-sulfonyl]-isobutyl-amino}-propyl)-carbamic acid hexahydro-furo[2,3-b]furan-3-yl ester |
| (1-Benzyl-2-hydroxy-3-{isobutyl-[3-(2-methoxy-benzylidene)-2-oxo-2,3-dihydro-1H-indole-5-sulfonyl]-amino}-propyl)-carbamic acid hexahydro-furo[2,3-b]furan-3-yl ester | (1-Benzyl-3-{isobutyl-[3-(5-methyl-furan-2-ylmethylene)-2-oxo-2,3-dihydro-1H-indole-5-sulfonyl]-amino}-2-phosphonooxy-propyl)-carbamic acid hexahydro-furo[2,3-b]furan-3-yl ester |
| (1-Benzyl-2-hydroxy-3-{[3-(4-hydroxy-3-methoxy-benzylidene)-2-oxo-2,3-dihydro-1H-indole-5-sulfonyl]-isobutyl-amino}-propyl)-carbamic acid hexahydro-furo[2,3-b]furan-3-yl ester | 4-(5-{[3-(Hexahydro-furo[2,3-b]furan-3-yloxycarbonylamino)-2-hydroxy-4-phenyl-butyl]-isobutyl-sulfamoyl}-2-oxo-1,2-dihydro-indol-3-ylidenemethyl)-benzoic acid | the N-oxides and salts thereof and their stereoisomeric forms.

The compounds of formula (I) can generally be prepared using procedures analogous to those procedures described in WO 95/06030, WO 96/22287, WO 96/28418, WO 96/28463, WO 96/28464, WO 96/28465 and WO 97/18205.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

Scheme A-1

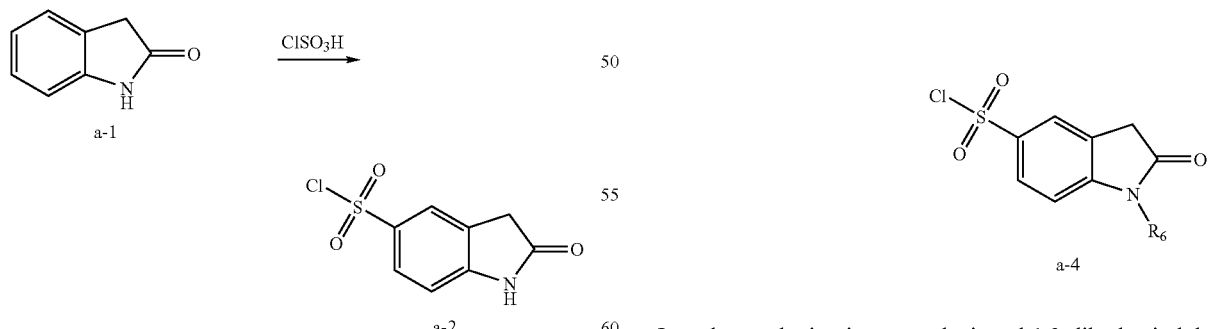

Intermediates of formula (a-2) can be prepared by reacting 1,3-dihydro-indol-2-one (a-1) with chlorosulphonic acid at an elevated temperature, suitably ranging between 50 and 60° C., and stirring the resulting intermediate.

Scheme A-2

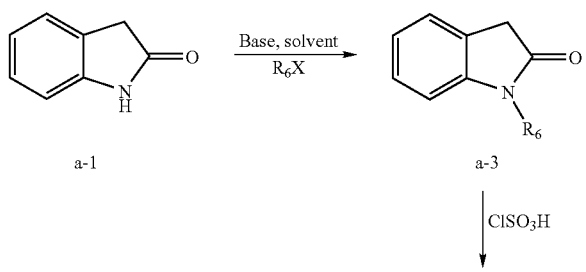

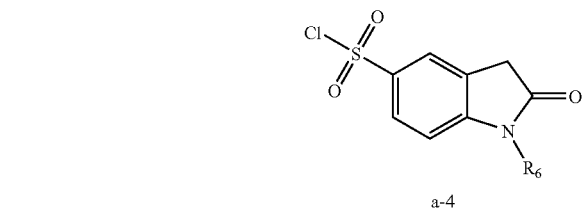

In order to obtain nitrogen substituted 1,3-dihydro-indol-2-ones of formula (a-3), 1,3-dihydro-indol-2-one can be reacted with an activated alkylderivative $R_6X$, such as an alkylhalide in a suitable aprotic polar solvent and in the presence of a base. Intermediates of formula a-4 can then be prepared starting from intermediates a-3 according to scheme A-1.

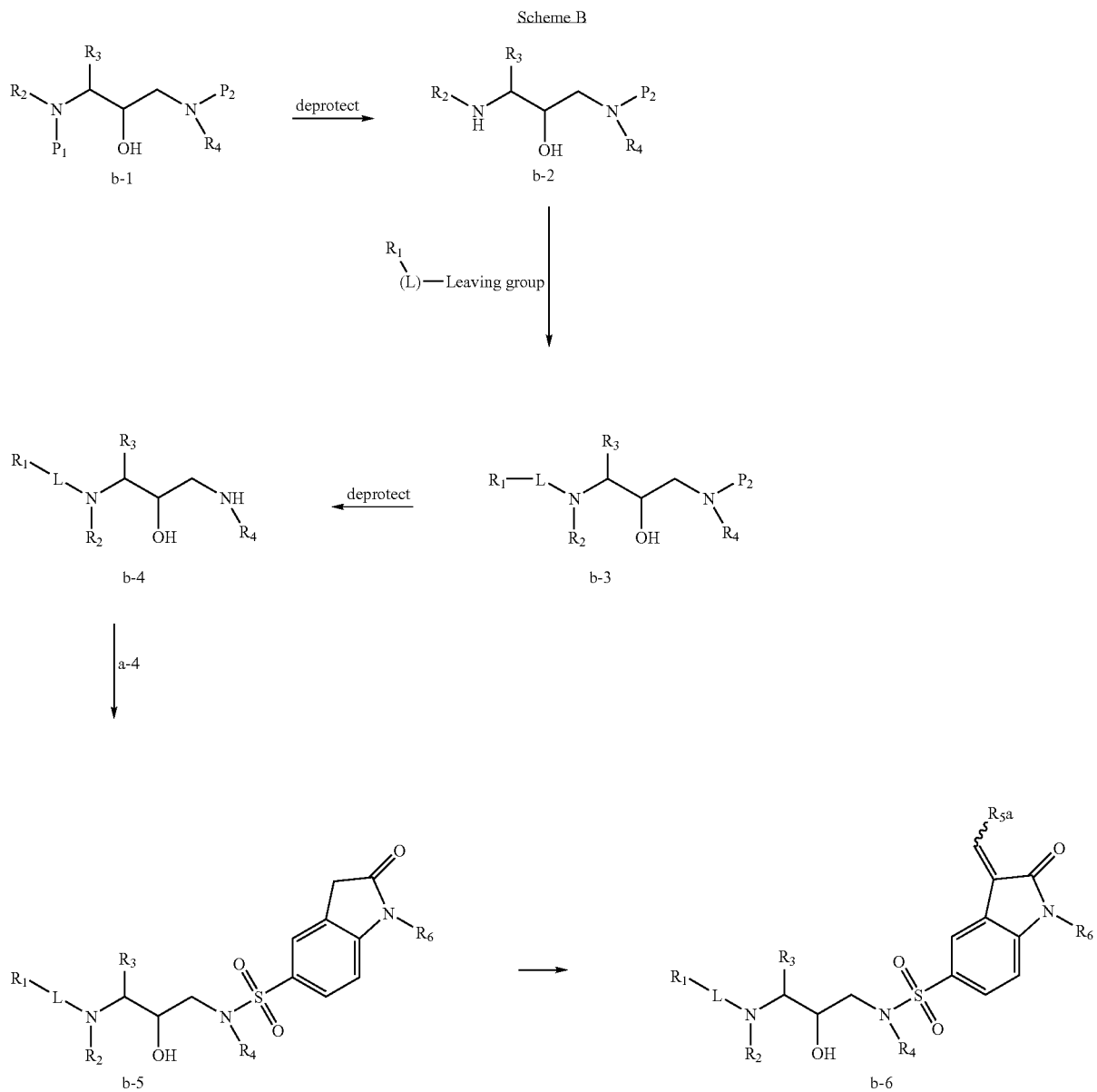

Scheme B

Preparation of b-1

This intermediate may be prepared according to the procedures outlined in WO 97/18205.

Preparation of b-2

Intermediate b-1 was stirred in an organic solvent in the presence of a catalyst such as Pd/C or Pd/OH under an hydrogen atmosphere. Under these conditions protecting group $P_1$ is removed.

Preparation of b-3.

To intermediate b-2, in an organic solvent, was added $R_1$-(L)-(leaving group) and a base. Alternatively, $R_1$-(L)-(leaving group) may be added in the presence of 1-(3-dimethylaminopropyl)-3-ethylcarbodiimide hydrochloric acid (EDC) and 1-hydroxybenzotriazole (HOBT) in an organic solvent. The reaction mixture was stirred 6 to 24 hours at temperatures ranging from 15 to 40° C. and the solvent was evaporated.

Preparation of b-4.

An alcoholic solution of intermediate b-3; was acidified to remove protecting group $P_2$. The mixture was stirred during 6 to 24 hours at temperatures ranging from 15 to 40° C., whereafter an organic solvent was added. The pH of the mixture was neutralized and subsequently washed with brine. The organic layer was dried and concentrated to yield intermediate b-4.

Preparation of b-5

Intermediate a-4 was added to a mixture of intermediate b-4 in an organic solvent and in the presence of an amine. The mixture was stirred at temperatures ranging from 15 to 40° C. for 4-24 hours and washed with a alkaline solution. The organic layer was dried and the solvent was evaporated.

Preparation of b-6

Reaction of intermediate b-5 with aldehydes ($R_{5a}$-C(=O)—H) results in the generation of b-6. The reaction is suitably performed in alcohols in the presence of an organic base at elevated temperatures ranging from 50° C. to reflux temperature.

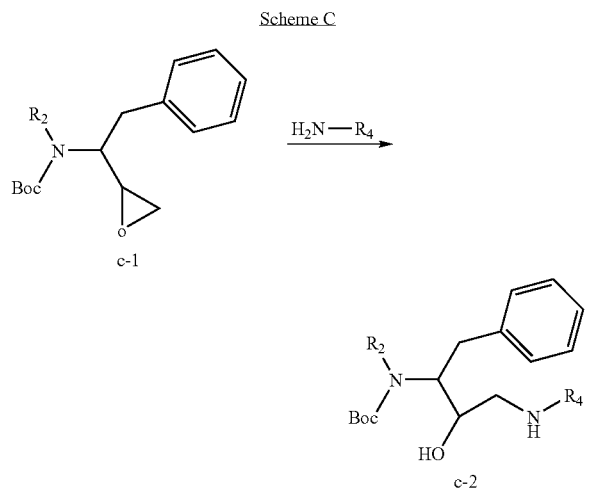

Scheme C c-1 c-2

Intermediate c-2, may be prepared by adding an amine of formula $H_2N-R_4$ to an intermediate c-1 in a suitable solvent such as isopropanol.

In scheme D, enantiomerically pure compounds of formula c-2 are only obtained if c-1 is enantiomerically pure. If c-1 is a mixture of stereoisomers, than c-2 will also consist of a mixture of stereoisomers.

DETAILED DESCRIPTION OF THE SYNTHESIS

1. Scheme A-1

A mixture of 46 ml chlorosulfonic acid and 10 g of 1,3-dihydro-indol-2-one (a-1) was heated to 50° C. during 12 hours. After cooling down to room temperature, the mixture was poured on ice and water and extracted with dichloromethane. The organic layer was separated, dried over $MgSO_4$ and the solvent was evaporated to yield 16.33 g (94%) of intermediate a-2 (2-oxo-2,3-dihydro-1H-indole-5-sulfonyl chloride).

2. Scheme A-2

In order to obtain nitrogen substituted 1,3-dihydro-indol-2-ones of formula (a-3), 1,3-dihydro-indol-2-one can be reacted with an activated alkylderivative $R_6X$, such as an alkylhalide in a suitable aprotic polar solvent solvent such as tetrahydrofuran (THF), dimethylformamide (DMF), dichloremethane (DCM) and in the presence of a base such as NaH, potassium carbonate or sodium carbonate. The mixture was stirred at room temperature (RT) and activated alkyls such as alkyl halide or acyl halide were added ($R_6-X$, wherein X is a halogen, suitably selected from Cl, I, Br; $R_6$ is selected from $-C_{1-6}$alkyl, $-C(=O)-C_{1-6}$alkyl, $-CH_2-C(=O)O-C_{1-6}$alkyl). The reaction mixture was stirred overnight at RT. Then water was added and the mixture was extracted with a suitable solvent and dried on magnesium sulphate. Intermediate a-3 was isolated by crystallisation or purification on silica gel. Intermediate a-4 was obtained according to the procedure outlined in Scheme A-1

3. Scheme B 3.1 Preparation of b-1

This intermediate may be prepared according to the procedures outlined in WO 97/18205.

3.2 Preparation of b-2

The mixture of intermediate b-1 in the presence of Pd/C in alcohols and or Pd/OH in cyclohexene or 1,3-cyclohexadiene was stirred overnight in a hydrogen atmosphere to remove protecting group $P_1$. For the purpose of the synthesis of the compounds of the present invention, $R_2$ at this stage of the synthesis, may also be a protecting group $P_1$. A preferred protecting group is benzyl, more preferable $P_1$ and $R_2$ are both benzyl, thus forming a dibenzyl moiety. Suitable alcohols for said reaction are e.g. MeOH, EtOH, isopropanol. The mixture was filtered and the solvent was evaporated to yield intermediate b-2.

3.3 Preparation of b-3.

To intermediate b-2, in an organic solvent, was added $R_1$-(L)-(leaving group) and a base. This reaction is a preferred route to generate carbamates. Alternatively, $R_1$-(L)-(leaving group) may be added in the presence of 1-(3-dimethylaminopropyl)-3-ethylcarbodiimide hydrochloric acid (EDC) and 1-hydroxybenzotriazole (HOBT) or an alcohol such as tertbutanol in a suitable solvent such as dichloromethane. Using the alternative strategy amides may be obtained. The reaction mixture was stirred overnight at RT and the solvent evaporated. The intermediate was purified on silica gel.

3.4 Preparation of b-4.

A mixture of intermediate b-3, in alcohols such as methanol, ethanol or isopropanol, was acidified (e.g. by the addition of HCl) to remove protecting group $P_2$. Suitable protecting groups are e.g. boc, Fmoc, Cbz. A preferred protecting group is boc. The mixture was stirred over night at RT. Then an organic solvent was added. Suitable solvents are e.g. ethylacetate, acetonitrile, aceton, cyclohexane, chloroform, toluene. The pH of the mixture was neutralized and subsequently washed with brine. Neutralization can suitably be done by sodium carbonate. The organic layer was dried over $MgSO_4$ and concentrated to yield intermediate b-4.

3.5 Preparation of b-5 a4 was added to a mixture of intermediate b-4 in an organic solvent and in the presence of an amine. Ethylacetate, acetonitrile, aceton, cyclohexane, chloroform and toluene are examples of suitable organic solvents. Amines are suitably selected from e.g. triethylamine, di-isopropylamine. The mixture was stirred at RT for 6–18 hours and washed with a solution of sodium bicarbonate and subsequently with brine. The organic layer was dried over MgSO4 and the solvent was evaporated. The compound was purified on silica gel.

3.6 Preparation of b-6

Reaction of intermediate b-5 with aldehydes ($R_{5a}-C(=O)-H$) results in the generation of b-6. The reaction is suitably performed in alcohols in the presence of an organic base e.g. pipiridine and at temperatures ranging from 65–100° C.

4. Preparation of Compound 7
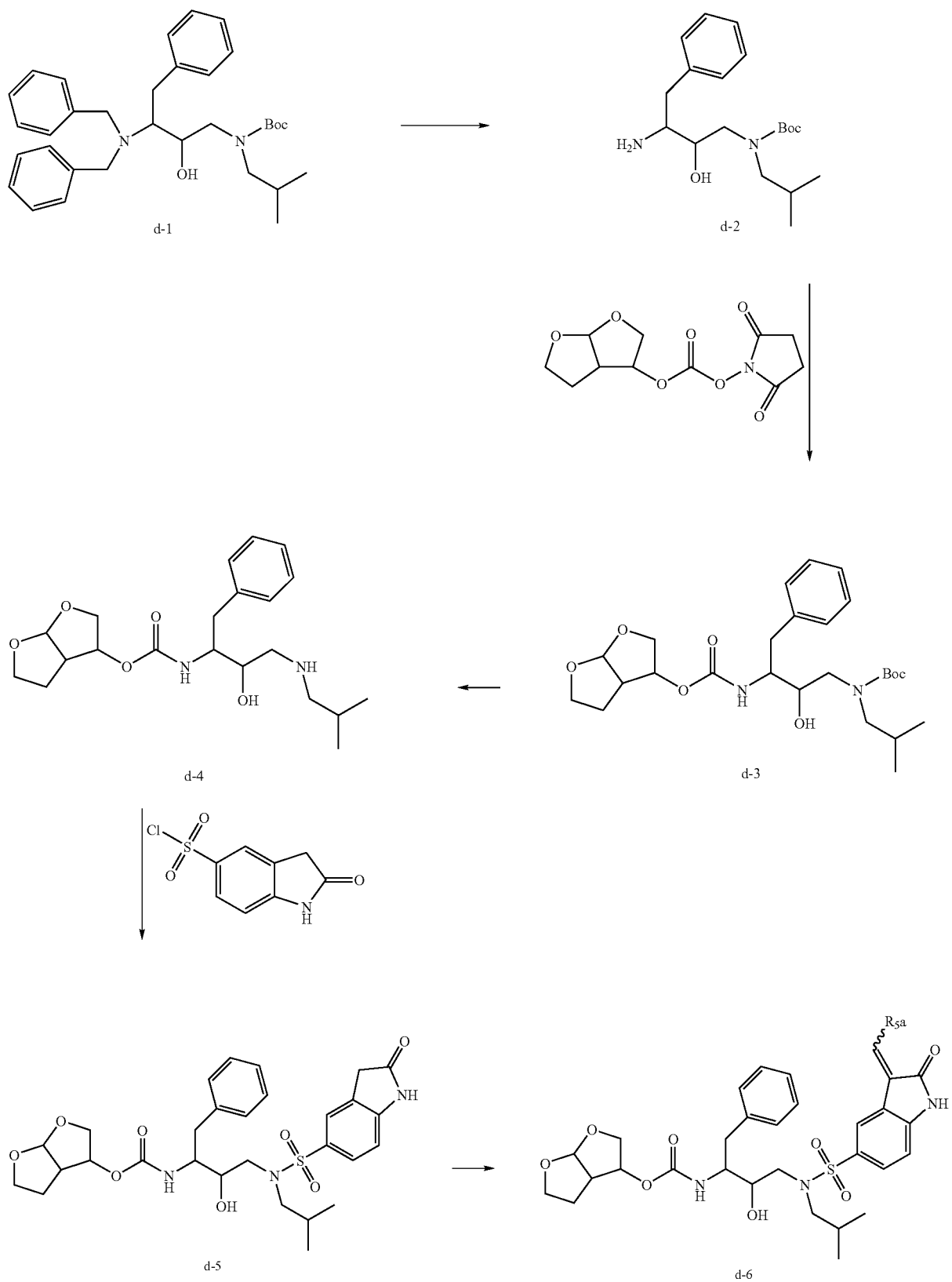

4.1 Preparation of d-2.

The mixture of 76.9 g of intermediate d-1 in MeOH and 5 g of Pd/C 10% was stirred overnight in a hydrogen atmosphere. The mixture was filtered using a filter such as celite and the solvent was evaporated to yield 48 g (96%) of intermediate d-2 (tert-butyl N-[3-amino-2-hydroxy-4-plenylbutyl]-N-isobutylcarbamate).

4.2 Preparation of d-3.

To a mixture of 7 g of intermediate d-2 in 300 ml of dichloromethane (DCM) was added 5.63 g of 1-[[(3R,3aS,6aR)-hexahydrofuro[2,3-b]furan-3-yl]oxycarbonyloxy]-2,5-pyrrolidinedione (prepared according to the procedure described in WO9967417) and 2.1 g of triethylamine. The reaction mixture was stirred overnight at RT and the solvent evaporated. The compound was purified on silica gel yielding 9 g (88%) of intermediate c-3 (Hexahydrofuro[2,3-b]furan-3-yl N-{1-benzyl-3-[(tertbutoxycarbonyl) (isobutyl)amino]-2-hydroxypropyl}carbamate).

4.3 Preparation of d-4.

To a mixture of 9 g of intermediate d-3 in 200 ml of ethanol was added drop wise a solution of hydrochloric acid (e.g. 6N HCl) in isopropanol. The mixture was stirred over night at RT. 300 ml ethylacetate was added and the mixture was washed with sodium bicarbonate solution 3 times and with brine. The organic layer was dried over MgSO4 and concentrated to yield 5.5 g (77%) of intermediate d-4 (Hexahydrofuro[2,3-b]furan-3-yl N-[1-benzyl-2-hydroxy-3-(isobutylamino)propyl]carbamate.

4.4 Preparation of d-5

To a mixture of 3.34 g of compound d-4 in DCM 100 ml and 1.72 g triethyl amine, 2.4 g 2-oxo-2,3-dihydro-1H-indole-5-sulfonyl chloride was added. The mixture was stirred at room temperature for 12 hours and washed with a solution of sodium bicarbonate and with brine. The organic layer was dried over MgSO4 and the solvent was removed. The compound was purified on silica gel yielding 4 g (80%) of intermediate c-5 (Hexahydrofuro[2,3-b]furan-3-yl N-(1-benzyl-2-hydroxy-3-{isobutyl[(2-oxo-2,3-dihydro-1H-indol-5-yl)sulfonyl]amino}propyl}carbamate)(compound 21).

4.5 Preparation of d-6 (Compound 7)

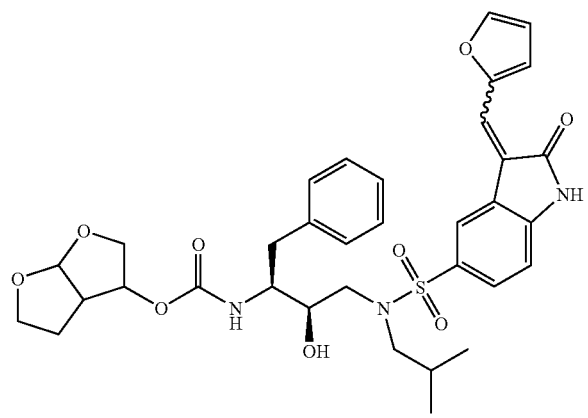

To a mixture of 1 g of intermediate d-5 in 40 ml of ethanol and 217 mg piperidine, 206 mg furfuraldehyd was added. The mixture was stirred at 85° C. for 6 hours. Water was added and the mixture was extracted with ethyl acetate. The organic layer was dried over MgSO4 and the solvent was removed. The compound was purified on silica gel yielding 1.1 g (95%) of compound 7 (d-6)(Hexahydrofuro[2,3-b]furan-3-yl N-{1-benzyl-3-[({3-[(E)-2-furylmethylidene]-2-oxo-2,3-dihydro-1H-indol-5-yl}sulfonyl) (isobutyl)amino]-2-hydroxypropyl}carbamate) in 70/30 E/Z mixture observed by NMR.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (I). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their favorable pharmacological properties, particularly their activity against multi-drug resistant HIV protease enzymes, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic central nervous system (CNS) diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I) or any subgroup thereof in the manufacture of a medicament for treating or combating infection or disease associated with multi-drug resistant retrovirus infection in a mammal, in particular HIV-1 infection. Thus, the invention also relates to a method of treating a retroviral infection, or a disease associated with multi-drug resistant retrovirus infection comprising administering to a mammal in need thereof an effective amount of a compound of formula (I) or a subgroup thereof.

In another preferred embodiment, the present invention relates to the use of formula (I) or any subgroup thereof in the manufacture of a medicament for inhibiting a protease of a multi-drug resistant retrovirus in a mammal infected with said retrovirus, in particular HIV-1 retrovirus.

In another preferred embodiment, the present invention relates to the use of formula (I) or any subgroup thereof in the manufacture of a medicament for inhibiting multi-drug resistant retroviral replication, in particular HIV-1 replication.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retioviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, 5-helix, D-peptide ADS-J1; co-receptor binding inhibitors, such as, for example, AMD 3100, AMD-3465, AMD7049, AMD3451 (Bicyclams), TAK 779; SHC-C (SCH351125), SHC-D, PRO-140RT inhibitors, such as, for example, foscarnet and prodrugs; nucleoside RTIs, such as, for example, AZT, 3TC, DDC, DDI, D4T, Abacavir, FTC, DAPD, dOTC, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPCO82, DPCO83, calanolide A, SJ-1366, TSAO, 4"-deaminated TSAO, MV150, MV026048; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMC-114, maslinic acid, U-140690; glycosylation inhibitors, such as, for example, castanospermine, deoxynojirimycine.

The combination may provide a synergistic effect, wherein viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, wherein the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, sequentially or independently of each other. Alternatively, such combination may be administered as a single formulation, wherein the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm.

Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition wherein the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The route of administration may depend on the condition of the subject, co-medication and the like.

Another aspect of the present invention concerns a kit or container comprising a compound of formula (I) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K et al. *Antimicrob Agents Chemother,* 1998; 42(2):269–276, incorporated by reference).

Interestingly, the compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond. Reactive groups will generally be stable in an aqueous environment and will usually be carboxy, phosphoryl, or convenient acyl group, either as an ester or a mixed anhydride, or an imidate, or a maleimidate thereby capable of forming a covalent bond with functionalities such as an amino group, a hydroxy or a thiol at the target site on for example blood components such as albumine. The compounds of the present invention may be linked to maleimide or derivatives thereof to form conjugates.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight co-medication and individual responsiveness of the human or animal to be treated and on whether the therapy is acute or prophylactic. Customarily, the daily dose of a compound of formula (I) in the case of administration to a patient approximately 75 kg in weight is 1 mg to 1 g, preferably 3 mg to 0.5 g. The dose can be administered in the form of an individual dose, or divided into several, e.g. two, three, or four, individual doses.

Experimental Part

Preparation of the compounds of formula (I) and their intermediates

TABLE 1

Compounds of the present invention prepared according to the methods described above. If no stereochemistry is indicated, the compound is present as a racemic mixture. The wavy bond indicates that the $R_a$ substituent may be in cis or trans position or in a mixture thereof.

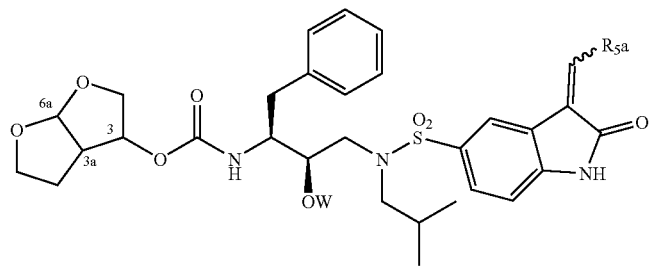

| NO | $R_{5a}$ | $pEC_{50}$ | W | Stereochemistry/salts |
|----|----------|------------|-----|----------------------|
| 1  |          | 8.5        | —H  | (3R, 3aS, 6aR)/base  |
| 2  |          | 8.07       | —H  | (3R, 3aS, 6aR)/base  |
| 3  |          | 7.94       | —H  | (3R, 3aS, 6aR)/base  |

TABLE 1-continued

Compounds of the present invention prepared according to the methods described above. If no stereochemistry is indicated, the compound is present as a racemic mixture. The wavy bond indicates that the $R_a$ substituent may be in cis or trans position or in a mixture thereof.

| NO | $R_{5a}$ | $pEC_{50}$ | W | Stereochemistry/salts |
|----|----------|------------|---|----------------------|
| 4 | 1-methylpyrrol-2-yl | 7.81 | —H | (3R, 3aS, 6aR)/base |
| 5 | (CH₃CH₂)₂CH— | 7.78 | —H | (3R, 3aS, 6aR)/base |
| 6 | (CH₃)₂CH— | 7.71 | —H | (3R, 3aS, 6aR)/base |
| 7 | furan-2-yl | 7.71 | —H | (3R, 3aS, 6aR)/base |
| 8 | 4-methoxyphenyl | 7.7 | —H | (3R, 3aS, 6aR)/base |
| 9 | 4-(pyridin-2-yl)phenyl | 7.64 | —H | (3R, 3aS, 6aR)/base |
| 10 | 2,4,6-trimethyl-3-hydroxyphenyl | 7.6 | —H | (3R, 3aS, 6aR)/base |
| 11 | 4-(dimethylamino)phenyl | 7.36 | —H | (3R, 3aS, 6aR)/base |
| 12 | 1H-indol-2-yl | 7.26 | —H | (3R, 3aS, 6aR)/base |

TABLE 1-continued

Compounds of the present invention prepared according to the methods described above. If no stereochemistry is indicated, the compound is present as a racemic mixture. The wavy bond indicates that the $R_a$ substituent may be in cis or trans position or in a mixture thereof.

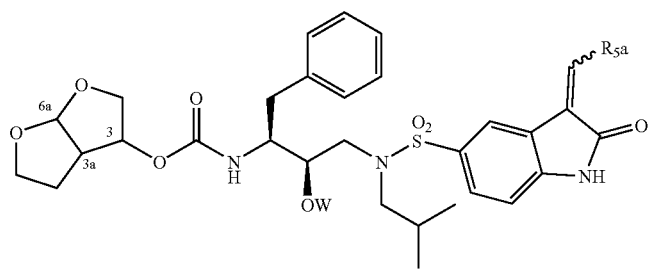

| NO | $R_{5a}$ | $pEC_{50}$ | W | Stereochemistry/salts |
|---|---|---|---|---|
| 13 | 5-methylfuran-2-yl-CH$_2$-O-C(O)-CH$_3$ | 7.25 | —H | (3R, 3aS, 6aR)/base |
| 14 | phenyl | 7.23 | —H | (—)/base |
| 15 | 4-(N,N-diethylamino)-3-hydroxyphenyl | 7.19 | —H | (3R, 3aS, 6aR)/base |
| 16 | 2-hydroxyphenyl | 7.15 | —H | (3R, 3aS, 6aR)/base |
| 17 | 2-methoxyphenyl | 7.11 | —H | (3R, 3aS, 6aR)/base |
| 18 | 3-methoxy-4-hydroxyphenyl | 6.57 | —H | (3R, 3aS, 6aR)/base |
| 19 | 5-methylfuran-2-yl | 6.52 | —PO$_3$H$_2$ | (3R, 3aS, 6aR)/base |
| 20 | 4-carboxyphenyl | 6.05 | —H | (3R, 3aS, 6aR)/base |

TABLE 1-continued

Compounds of the present invention prepared according to the methods described above. If no stereochemistry is indicated, the compound is present as a racemic mixture. The wavy bond indicates that the $R_a$ substituent may be in cis or trans position or in a mixture thereof.

| NO | $R_{5a}$ | $pEC_{50}$ | W | Stereochemistry/salts |
|----|----------|------------|---|----------------------|

Compound 21

Antiviral Analyses:

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

Cellular Assay Experimental Method:

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor. Wherever results are reported as e.g. $pEC_{50}$ or $pCC_{50}$ values, the result is expressed as the negative logarithm of the result expressed as $EC_{50}$ or $CC_{50}$ respectively.

Antiviral Spectrum:

Because of the increasing emergence of drug resistant HIV strains, the present compounds were tested for their potency against clinically isolated HIV strains harboring several mutations (Table 2 and 3). These mutations are associated with resistance to protease inhibitors and result in viruses that show various degrees of phenotypic cross-resistance to the currently commercially available drugs such as for instance saquinavir, ritonavir, nelfinavir, indinavir and amprenavir.

TABLE 2

List of mutations present in the protease gene of the HIV strains (A to F) used.

| | |
|---|---|
| A | V003I, L010I, V032T, L033M, E035D, S037Y, S037D, M046I, R057R/K, Q058E, L063P, K070T, A071V, I072V, I084V, L089V |
| B | V003I, L010I, K020R, E035D, M036I, S037N, Q058E, I062V, L063P, A071V, I072M, G073S, V077I, I084V, I085V, L090M |
| C | V003I, L010I, I015V, L019I, K020M, S037N, R04IK, I054V, Q058E, L063P, A071V, I084V, L090M, I093L |

TABLE 2-continued

List of mutations present in the protease gene of the HIV strains (A to F) used.

D  V003I, L010L/I, I013V, L033I, E035D, M036I, M046L, K055R, R057K, L063P, I066F, A071V, I084V, N088D, L090M
E  V003I, L010I, V011I, A022V, L024I, E035D, M036I, S037T, R041K, I054V, I062V, L063P, A071V, I084V
F  L010F, M046I, M071V, I084V

Results:

As a measure of the broad spectrum activity of the present compounds, the fold resistance (FR), defined as FR=$EC_{50}$ (mutant strain)/$EC_{50}$(HIV-1 strain LAI), was determined. Table 3 shows the results of the antiviral testing in terms of fold resistance. As can be seen in this table, the present compounds are effective in inhibiting a broad range of mutant strains: Column A FR value towards mutant A, Column B: FR towards mutant B, Column C: FR towards mutant C, Column D: FR towards mutant D, Column E: FR towards mutant E, Column F: FR towards mutant F. The toxicity (Tox) is expressed as the $pCC_{50}$ value as determined with mock transfected cells. Column WT displays the pEC50 value against wild type HIV-LAI strain.

TABLE 3

Results of the toxicity testing and the resistance testing against mutant strains A to F (expressed as FR).

| No | A | B | C | D | E | F | Tox | WT |
|---|---|---|---|---|---|---|---|---|
| 1 | 4.3 | 8.7 | 2.1 | 2.0 | 6.2 | 10 | 4.9 | 8.5 |
| 2 | 1.7 | 3.6 | 1 | 3.8 | 3.1 | 3.9 | 4.7 | 8.01 |
| 3 | 3.0 | 3.8 | 2.6 | 3.0 | 7.1 | 6.8 | 4 | 7.9 |
| 4 | 2.3 | 1.9 | 1.7 | 1.9 | 2.4 | 2.0 | 4 | 7.8 |
| 5 | 1.9 | 8.3 | 2.0 | 2.0 | 4.2 | 6.5 | 4.2 | 7.8 |
| 6 | 2.5 | 7.1 | 1.6 | 1.4 | 2.0 | 7.9 | 4.3 | 7.7 |
| 7 | 1.8 | 2.6 | 1.7 | 2.4 | 5.9 | 1.9 | 4.1 | 7.7 |
| 8 | 1.7 | 5.0 | 1.5 | 1.5 | 2.0 | 1.7 | 4.2 | 7.7 |
| 9 | 1.3 | 6.2 | 2.0 | 1.9 | 3.0 | 6.3 | 4.2 | 7.6 |
| 10 | 1.4 | 1.3 | 1.3 | 1.3 | 1.5 | 2.0 | 4 | 7.6 |
| 11 | 1.5 | 4.7 | 1.4 | 3.4 | 3.4 | 3.5 | 4 | 7.4 |
| 21 | 1.0 | 1.1 | 0.7 | 0.33 | 0.56 | 1.2 | 4.0 | 6.8 |

In Vitro Pharmacokinetic Studies

The permeability of different compounds is evaluated according to a Caco-2 test protocol as described by Augustijns et al. (Augustijns et al. (1998). *Int. J. of Pharm*, 166, 45–54) whereby, Caco-2 cells at cell passage number between 32 and 45 are grown in 24-well cell culture plates for 21 to 25 days. The integrity of the cell monolayer is checked by measuring the transepithelial electrical resistance (TEER). The test is performed at pH 7.4 and at 100 µM donor compound concentration.

The equilibrium solubility in simulated gastrointestinal solutions under thermodynamic conditions is a good measure for the solubility profile of the compound in the stomach and the different parts of the intestine. Simulated gastric fluid (SGF) (without pepsin) is set at pH of 1.5. Simulated intestinal fluids (SIF) (without bile salts) are set at pH 5, pH 6.5, pH 7 and pH 7.5. The experimental protocol uses 96-well flat-bottom microplates in which 1 mg of compound is added per well (stock solution in methanol) and evaporated to dryness. The compounds are resolubilized in SGF and SIF and incubated overnight on a horizontal shaking device at 37° C. After filtration, the compound concentrations are determined by UV-spectrophotometry.

Oral Availability in the Rat and the Dog

The compounds are formulated as a 20 mg/ml solution or suspension in DMSO, PEG400 or cyclodextin 40% (CD40%) in water. For most experiments in the rat, three dosing groups are formed: 1/single intraperitoneal dose at 20 mg/kg using the DMSO formulation; 2/single oral dose at 20 mg/kg using the PEG400 formulation and 3/single oral dose at 20 mg/kg using the cyclodextrin formulation. Blood was sampled at regular time intervals after dosing and drug concentrations in the serum were determined using a LC-MS bioanalytical method.

Boosting the Systemic Bioavailability

With the described type of compounds (protease-inhibitors), it is known that inhibition of the metabolic degradation processes can markedly increase the systemic availability by reducing the first-pass metabolism in the liver and the metabolic clearance from the plasma. This 'boosting' principle can be applied in a clinical setting to the pharmacological action of the drug. This principle can be also explored both in the rat or the dog by simultaneous administration of a compound that inhibits the Cyt-p450 metabolic enzymes. Known blockers are for example ritonavir and ketoconazole.

Protein Binding Analyses

Human serum proteins like albumin (HSA) or α-1 acid glycoprotein (AAG) are known to bind many drugs, resulting in a possible decrease in the effectiveness of those compounds. In order to determine whether the present compounds would be adversely affected by this binding, the anti-HIV activity of the compounds was measured in the presence of human serum, thus evaluating the effect of the binding of the protease inhibitors to those proteins.

MT4 cells are infected with HIV-1 LAI at a multiplicity of infection (MOI) of 0.001–0.01 $CCID_{50}$ (50% cell culture infective dose per cell, $CCID_{50}$). After 1 h incubation, cells are washed and plated into a 96 well plate containing serial dilutions of the compound in the presence of 10% FCS (foetal calf serum), 10% FCS+1 mg/ml AAG ($\alpha_1$-acid glycoprotein), 10% FCS+45 mg/ml HSA (human serum albumin) or 50% human serum (HS). After 5 or 6 days incubation, the $EC_{50}$ (50% effective concentration in cell-based assays) is calculated by determining the cell viability or by quantifying the level of HIV replication. Cell viability is measured using the assay described above. Into a 96 well plate containing serial dilutions of the compound in the presence of 10% FCS or 10% FCS+1 mg/ml AAG, HIV (wild type or resistant strain) and MT4 cells are added to a final concentration of 200–250 $CCID_{50}$/well and 30,000 cells/well, respectively. After 5 days of incubation (37° C., 5% $CO_2$), the viability of the cells is determined by the tetrazolium colorimetric MTT (3-[4,5-Dimethylthiazol-2-yl]-2,5-diphenyltetrazolium bromide) method (Pauwels et al. J. Virol. Methods 1988, 20, 309321).

Formulation

Active ingredient, in casu a compound of formula (I), was dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, were dissolved in organic solvents such as ethanol, methanol methylene chloride. Suitably the polymer was dissolved in ethanol. The polymer and compound solutions were mixed and subsequently spray dried. The ratio of compound/polymer was selected from 1/1 to 1/6. Intermediate ranges were 1/1.5 and 1/3. A suitable ratio was 1/6. The spraydried powder, a solid dispersion, is subsequently filled in capsules for administration. The drug load in one capsule ranges between 50 and 100 mg depending on the capule size used.

Film-Coated Tablets

Preparation of Tablet Core

A mixture of 100 g of active ingredient, in casu a compound of formula (I), 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methylcellulose in 75 ml of denaturated ethanol there was added a solution of 5 g of ethylcellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

The invention claimed is:

1. A compound having the formula

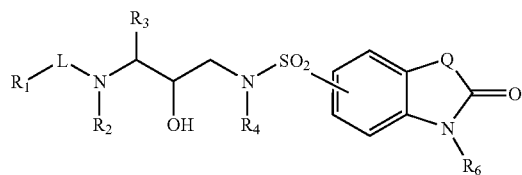

(I)

an N-oxide, salt, stereoisomeric form, racemic mixture, prodrug, or ester thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, or Het$^2C_{1-6}$alkyl;

$R_1$ may also be a radical of formula

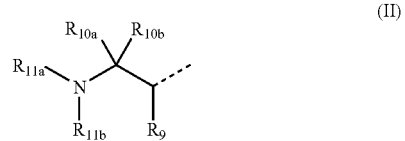

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-6}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are each independently selected from $C_{1-6}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl; wherein $R_9$, $R_{10a}$ and the carbon atoms to which they are attached may also form a $C_{3-7}$cycloalkyl radical; when L is —O—$C_{1-6}$alkanediyl-C(=O)— or —NR$_8$—$C_{1-6}$alkanediyl-C(=O)—, then $R_9$ may also be oxo;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$oxycarbonyl, Het$^2$oxycarbonyl, aryloxycarbonyl$C_{1-4}$alkyl, aryl$C_{1-4}$ lkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$ alkylcarbonyloxy, $C_{1-4}$alkylcarbonyloxy, aryl$C_{1-4}$ alkylcarbonyloxy, arylcarbonyloxy, aryloxycarbonyloxy, Het$^1$carbonyl, Het$^1$carbonyloxy, Het$^1C_{1-4}$alkyloxycarbonyl, Het$^2$ carbonyloxy, Het$^2C_{1-4}$alkylcarbonyloxy, Het$^2C_{1-4}$ alkyloxycarbonyloxy or $C_{1-6}$alkyl optionally substituted with aryl, aryloxy, Het$^2$ or hydroxy; wherein the substituents on the amino groups are each independently selected from $C_{1-6}$alkyl, aryl, aryl$C_{1-4}$ alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-6}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$ alkyl, Het$^1$, Het$^2$, Het$^1C_{1-4}$alkyl and Het$^2C_{1-4}$alkyl;

wherein $R_{11b}$ may be linked to the remainder of the molecule via a sulfonyl group;

t is, each independently, zero, 1 or 2;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$, wherein either the C(=O) group or the S(=O)$_2$ group is attached to the NR$_2$ moiety; and wherein each independently the $C_{1-6}$alkanediyl moiety may be optionally substituted with hydroxy, aryl, $Het^1$ or $Het^2$;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-6}$alkyl optionally substituted with one or more substituents each independently selected from aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, mono- or di($C_{1-4}$alkyl)aminosulfonyl, $C_{1-4}$alkylS($=$O)$_p$, hydroxy, cyano, halogen or amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

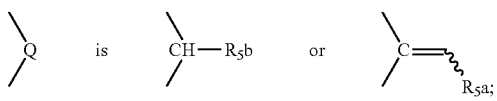

$R_{5a}$ and $R_{5b}$ are, each independently, selected from hydrogen, $C_{1-6}$alkyl, $C_{2-6}$alkenyl, $C_{2-6}$alkynyl, $C_{3-7}$cycloalkyl, aryl, $Het^1$, $Het^2$; wherein each of the substituents selected from $C_{1-6}$alkyl, $C_{2-6}$alkenyl, $C_{2-6}$alkynyl or $C_{3-7}$cycloalkyl, are optionally substituted on one or more carbon atoms with a substituent independently selected from the group consisting of amino, mono- or di($C_{1-4}$alkyl)amino, hydroxy, carboxyl, oxo, mercapto, halogen, cyanogen, nitro, $C_{1-4}$alkyloxy, $C_{1-4}$alkylcarbonyl, $C_{1-4}$alkylcarbonyloxy, $C_{1-4}$alkyloxycarbonyl, aryl, $C_{3-7}$cycloalkyl, $Het^1$, $Het^1$, $C_{1-4}$alkylcarbonyloxy, and $C_{1-4}$alkyloxycarbonyl;

$R_6$ is hydrogen or $C_{1-6}$alkyl optionally substituted on one or more carbon atoms with one or more substituents independently selected from the group consisting of amino, mono- or di($C_{1-4}$alkyl)amino, hydroxy, mercapto, oxo, cyanogen, nitro, halogen, carboxyl $C_{1-4}$alkyloxy, $C_{1-4}$alkylcarbonyl, $C_{1-4}$alkylcarbonyloxy, $C_{1-4}$alkyloxycarbonyl, $C_{3-7}$cycloalkyl, aryl, $Het^1$, $Het^2$; wherein each $C_{1-4}$alkyl may optionally be substituted by amino, mono- or di($C_{1-4}$alkyl)amino, hydroxy, mercapto, oxo, cyanogen, nitro, halogen, or carboxyl.

2. A compound according to claim 1 wherein $R_1$ is hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$, or $Het^2C_{1-6}$alkyl; wherein $Het^1$ is a monocyclic or bicyclic heterocycle having 5 to 10 ring members, which contains one or more heteroatom ring members each independently selected from nitrogen, oxygen or sulfur and which is optionally substituted on one or more carbon atoms.

3. A compound according to claim 1 wherein L is —O—$C_{1-6}$alkanediyl-C($=$O)—.

4. A compound according to claim 1 wherein
$R_{5a}$ and $R_{5b}$ are each independently selected from the group consisting of aryl, $Het^1$, $Het^2$ and $C_{1-6}$alkyl optionally substituted on one or more atoms with a substituent independently selected from the group consisting of amino, hydroxy, carboxyl, oxo, sulfhydryl, halogen, nitro, cyanogen, $C_{1-4}$alkyl, amino$C_{1-4}$alkyl, hydroxy$C_{1-4}$alkyl, halo$C_{1-4}$alkyl, $C_{1-4}$alkyloxy, $C_{1-4}$alkylcarbonyl, $C_{1-4}$alkylcarbonyloxy, $C_{1-4}$alkyloxycarbonyl, $C_{1-4}$alkylcarbonyloxy$C_{1-4}$alkyl, $C_{1-4}$alkyloxycarbonyl$C_{1-4}$alkyl, aryl, $C_{3-7}$cycloalkyl, $Het^1$ and $Het^2$; and $R_6$ is hydrogen.

5. A compound selected from the group consisting of:
(1-Benzyl-2-hydroxy-3-{isobutyl-[2-oxo-3-(1H-pyrrol-2-ylmethylene)-2,3-dihydro-1H-indole-5-sulfonyl]-amino}-propyl)-carbamic acid hexahydro-furo[2,3-b]furan-3-yl ester,
(1-Benzyl-2-hydroxy-3-{isobutyl-[3-(5-methyl-furan-2-ylmethylene)-2-oxo-2,3-dihydro-1H-indole-5-sulfonyl]-amino}-propyl)-carbamic acid hexahydro-furo[2,3-b]furan-3-yl ester,
(1-Benzyl-2-hydroxy-3-{isobutyl-[3-(5-methyl-thiophen-2-ylmethylene)-2-oxo-2,3-dihydro-1H-indole-5-sulfonyl]-amino}-propyl)-carbamic acid hexahydro-furo[2,3-b]furan-3-yl ester,
(1-Benzyl-2-hydroxy-3-{isobutyl-[3-(1-methyl-1H-pyrrol-2-ylmethylene)-2-oxo-2,3-dihydro-1H-indole-5-sulfonyl]-amino}-propyl)-carbamic acid hexahydro-furo[2,3-b]furan-3-yl ester,
(1-Benzyl-3-{[3-(2-ethyl-butylidene)-2-oxo-2,3-dihydro-1H-indole-5-sulfonyl]-isobutyl-amino}-2-hydroxy-propyl)-carbamic acid hexahydro-furo[2,3-b]furan-3-yl ester,
{1-Benzyl-2-hydroxy-3-[isobutyl-(3-isobutylidene-2-oxo-2,3-dihydro-1H-indole-5-sulfonyl)-amino]-propyl}-carbamic acid hexahydro-furo[2,3-b]furan-3-yl ester,
{1-Benzyl-3-[(3-furan-2-ylmethylene-2-oxo-2,3-dihydro-1H-indole-5-sulfonyl)-isobutyl-amino]-2-hydroxy-propyl}-carbamic acid hexahydro-furo[2,3-b]furan-3-yl ester,
(1-Benzyl-2-hydroxy-3-{isobutyl-[3-(4-methoxy-benzylidene)-2-oxo-2,3-dihydro-1H-indole-5-sulfonyl]-amino}-propyl)-carbamic acid hexahydro-furo[2,3-b]furan-3-yl ester,
(1-Benzyl-2-hydroxy-3-{isobutyl-[2-oxo-3-(4-pyridin-2-yl-benzylidene)-2,3-dihydro-1H-indole-5-sulfonyl]-amino}-propyl)-carbamic acid hexahydro-furo[2,3-b]furan-3-yl ester,
(1-Benzyl-2-hydroxy-3-{[3-(4-hydroxy-3,5-dimethyl-benzylidene)-2-oxo-2,3-dihydro-1H-indole-5-sulfonyl]-isobutyl-amino}-propyl)-carbamic acid hexahydro-furo[2,3-b]furan-3-yl ester,
(1-Benzyl-3-{[3-(4-dimethylamino-benzylidene)-2-oxo-2,3-dihydro-1H-indole-5-sulfonyl]-isobutyl-amino}-2-hydroxy-propyl)-carbamic acid hexahydro-furo[2,3-b]furan-3-yl ester,
(1-Benzyl-2-hydroxy-3-{[3-(1H-indol -2-ylmethylene)-2-oxo-2,3-dihydro-1H-indole-5-sulfonyl]-isobutyl-amino}-propyl)-carbamic acid hexahydro-furo[2,3-b]furan-3-yl ester,
Acetic acid 5-(5-{[3-(hexahydro-furo[2,3-b]furan-3-yloxycarbonylamino)-2-hydroxy-4-phenyl-butyl]-isobutyl-sulfamoyl}-2-oxo-1,2-dihydro-indol-3-ylidenemethyl)-furan-2-ylmethyl ester,
{1-Benzyl-3-[(3-benzylidene-2-oxo-2,3-dihydro-1H-indole-5-sulfonyl)-isobutyl-amino]-2-hydroxy-propyl}-carbamic acid hexahydro-furo[2,3-b]furan-3-yl ester,
(1-Benzyl-3-{[3-(4-diethylamino-3-hydroxy-benzylidene)-2-oxo-2,3-dihydro-1H-indole-5-sulfonyl]-isobutyl-amino}-2-hydroxy-propyl)-carbamic acid hexahydro-furo[2,3-b]furan-3-yl ester, (1-Benzyl-2-hydroxy-3-{[3-(2-hydroxy-benzylidene)-2-oxo-2,3-dihydro-1H-indole-5-sulfonyl]-isobutyl-amino}-propyl)-carbamic acid hexahydro-furo[2,3-b]furan-3-yl ester, (1-Benzyl-2-hydroxy-3-{isobutyl-[3-(2-methoxy-benzylidene)-2-oxo-2,3-dihydro-1H-indole-5-sulfonyl]-amino}-propyl)-carbamic acid hexahydro-furo[2,3-b]furan-3-yl ester, (1-Benzyl-2-hydroxy-3-{[3-(4-hydroxy-3-methoxy-benzylidene)-2-oxo-2,3-dihydro-1H-indole-5-sulfonyl]-isobutyl-amino}-propyl)-carbamic acid hexahydro-furo[2,3-b]furan-3-yl ester, (1-Benzyl-3-{isobutyl-[3-(5-methyl-furan-2-ylmethylene)-2-oxo-2,3-dihydro-1H-indole-5-sulfonyl]-amino}-2-phosphonooxy-propyl)-carbamic acid hexahydro-furo[2,3-b]furan-3-yl ester, 4-(5-{[3-(Hexahydro-furo[2,3-b]furan-3-yloxycarbonylamino)-2-hydroxy-4-phenyl-butyl]-isobutyl-sulfamoyl}-2-oxo-1,2-dihydro-indol-3-ylidenemethyl)-benzoic acid, and a N-oxides, salts and stereoisomeric forms thereof.

6. A pharmaceutical composition, comprising an effective amount of at least one compound as claimed in claim 1, and a pharmaceutically tolerable excipient.

7. A method of treating infection or disease associated with multi-drug resistant human immunodeficiency virus (HIV) retrovirus infection in a mammal, comprising administering an effective amount of at least one compound according to claim 1 to said mammal.

8. A pharmaceutical composition, comprising an effective amount of at least one compound as claimed in claim 2 and a pharmaceutically tolerable excipient.

9. A method of treating infection or disease associated with multi-drug resistant human immunodeficiency virus (HIV) retrovirus infection in a mammal, comprising administering an effective amount of at least one compound according to claim 2 to said mammal.

10. A pharmaceutical composition, comprising an effective amount of at least one compound as claimed in claim 5 and a pharmaceutically tolerable excipient.

11. A method of treating infection or disease associated with multi-drug resistant human immunodeficiency virus (HIV) retrovirus infection in a mammal, comprising administering an effective amount of at least one compound according to claim 5 to said mammal.

12. A pharmaceutical composition, comprising an effective amount of at least one compound as claimed in claim 1 and a pharmaceutically tolerable excipient.

13. A pharmaceutical composition, comprising an effective amount of at least one compound as claimed in claim 3 and a pharmaceutically tolerable excipient.

14. A pharmaceutical composition, comprising an effective amount of at least one compound as claimed in claim 4 and a pharmaceutically tolerable excipient.

15. A pharmaceutical composition, comprising an effective amount of at least one compound as claimed in claim 6 and a pharmaceutically tolerable excipient.

* * * * *